US010619134B2

(12) United States Patent
Dudakov et al.

(10) Patent No.: US 10,619,134 B2
(45) Date of Patent: Apr. 14, 2020

(54) USE OF BMP4 FOR THYMIC REGENERATION

(71) Applicant: Memorial Sloan-Kettering Cancer Center, New York, NY (US)

(72) Inventors: Jarrod Dudakov, Seattle, WA (US); Marcel Van Den Brink, New York, NY (US); Tobias Wertheimer, Freiburg (DE)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 0 days.

(21) Appl. No.: 15/499,124

(22) Filed: Apr. 27, 2017

(65) Prior Publication Data

US 2017/0292111 A1    Oct. 12, 2017

Related U.S. Application Data

(63) Continuation of application No. PCT/US2015/058095, filed on Oct. 29, 2015.

(60) Provisional application No. 62/086,928, filed on Dec. 3, 2014, provisional application No. 62/069,896, filed on Oct. 29, 2014.

(51) Int. Cl.
*A61K 38/03* (2006.01)
*C12N 5/071* (2010.01)
*A61K 38/18* (2006.01)
*C07K 14/51* (2006.01)
*C07K 14/005* (2006.01)
*C12N 5/10* (2006.01)

(52) U.S. Cl.
CPC ........ *C12N 5/0617* (2013.01); *A61K 38/1875* (2013.01); *C07K 14/005* (2013.01); *C07K 14/51* (2013.01); *C12N 5/10* (2013.01); *C12N 2501/155* (2013.01); *C12N 2710/10322* (2013.01)

(58) Field of Classification Search
CPC .. A61K 38/1875; C07K 14/005; C07K 14/51; C12N 2501/155; C12N 2710/10322; C12N 5/0617; C12N 5/10
See application file for complete search history.

(56) References Cited

U.S. PATENT DOCUMENTS

2004/0096971 A1    5/2004   Blackburn et al.
2010/0093081 A1    4/2010   Rafii et al.

FOREIGN PATENT DOCUMENTS

WO    2011139628    11/2011

OTHER PUBLICATIONS

Lombardo et al. Bone Morphogenetic Protein 4 Induces Differentiation of Colorectal Cancer Stem Cells and Increases Their Response to Chemotherapy in Mice. Gastroenterology. 2011;140:297-309.*
Bleul et al. BMP Signaling Is Required for Normal Thymus Development. The Journal of Immunology. 2005;175:5213-5221.*
Hager-Theodorides et al. "Bone Morphogenetic Protein 2/4 Signaling Regulates Early Thymocyte Differentiation," The Journal of Immunology, vol. 169, No. 10, pp. 5496-5504, Nov. 15, 2002.
Tsai et al. "BMP4 acts upstream of FGF in modulating thymic stroma and regulating thymopoiesis," Blood, vol. 102, No. 12, pp. 3947-3953, Aug. 21, 2003.
Patel et al. "Bmp4 and Noggin expression during early thymus and parathyroid organogenesis," Gene Expression Patterns, vol. 6, No. 8, pp. 794-799, Oct. 2, 2006.
Gossens et al. "Thymic progenitor homing and lymphocyte homeostasis are linked via S1P-controlled expression of thymic P-selectin/CCL25," The Journal of Experimental Medicine, vol. 206, No. 4, pp. 761-778, Mar. 16, 2009.
Wertheimer et al. "Production of BMP4 by endothelial cells is crucial for endogenous thymic regeneration," Science Immunology, vol. 3, No. 19, pp. eaal2736, Jan. 12, 2018.
Extended European Search Report for EP Application No. 15854018.7, dated Apr. 13, 2018, 10 pages.
International Search Report and Written Opinion of the International Searching Authority for PCT/US2015/58095 dated Dec. 30, 2015, 8 pages.
Gossens et al. "Thymic progenitor homing and lymphocyte homeostasis are linked via SIP-controlled expression of thymic P-selectin/CCL25," The Journal of Experimental Medicine, vol. 206, No. 4, pp. 761-778, Apr. 13, 2009.

* cited by examiner

*Primary Examiner* — Lynn Y Fan
(74) *Attorney, Agent, or Firm* — Heslin Rothenberg Farley & Mesiti P.C.

(57) ABSTRACT

The present disclosure describes methods to promote thymic regeneration following injury or damage to the thymus by administering to the thymus an effective amount of (1) bone morphogenetic protein 4 (BMP4), (2) thymus-derived endothelial cells that express BMP4 or (3) a combination of BMP4 and BMP4-secreting thymus-derived endothelial cells.

12 Claims, 45 Drawing Sheets

H

Untreated day 4 day 7 day 14

E

F

D

E

A

E

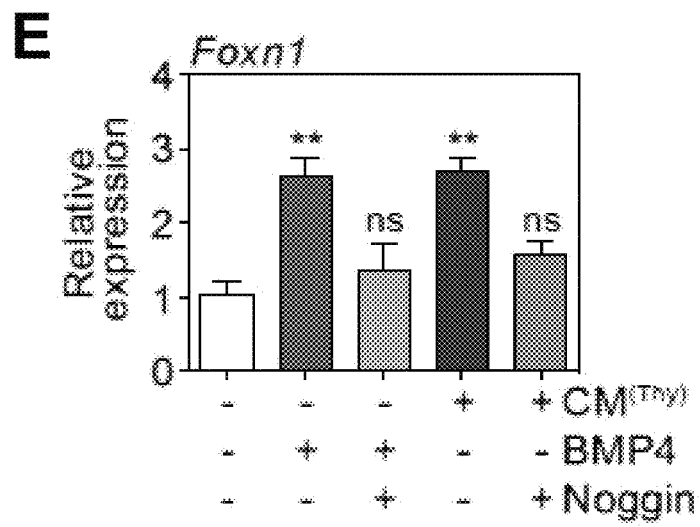
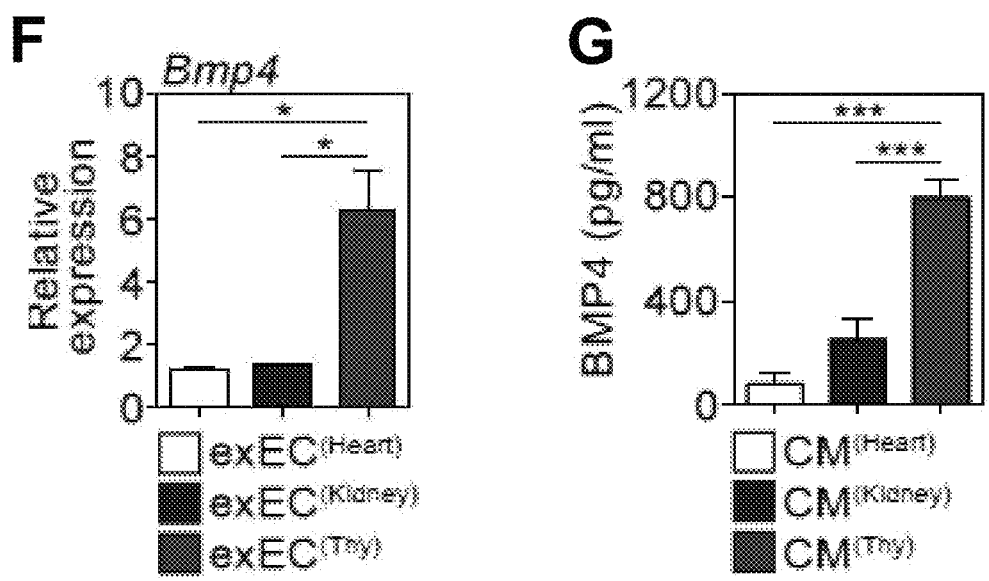
FIGURES 14E-14G

USE OF BMP4 FOR THYMIC REGENERATION

CROSS-REFERENCE TO RELATED APPLICATIONS

This application is a continuation of PCT/US2015/058095 filed on Oct. 29, 2015 and published as WO 2016/069911 on May 6, 2016, which claims the priority of U.S. provisional application No. 62/069,896 filed Oct. 29, 2014 and U.S. provisional application No. 62/086,928 filed Dec. 3, 2014; the entire contents of each are hereby incorporated in their entirety into the present disclosure.

STATEMENT REGARDING FEDERALLY SPONSORED RESEARCH OR DEVELOPMENT

This invention was made with U.S. Government support under grant number HL069929 from the National Institutes of Health. The government has certain rights in the invention.

TECHNICAL FIELD OF THE DISCLOSURE

The present invention relates generally to thymic regeneration and recovery from injury. More particularly, the present invention relates to the role of thymic endothelial cells (ECs) in thymopoiesis and thymic regeneration and provides a method of promoting thymic regeneration after thymic damage or injury.

BACKGROUND OF THE DISCLOSURE

Thymopoiesis is a complex process involving crosstalk between developing thymocytes and the non-hematopoietic stromal microenvironment, which includes thymic epithelial cells (TECs), fibroblasts and endothelial cells (ECs). Despite its importance, the thymus is exquisitely sensitive to damage caused by stress, infection, age, and cytoreductive treatments such as chemotherapy and radiation therapy. Continuous generation of adaptive immune diversity is dependent on T cell development in the thymus. However, despite this sensitivity to injury, the thymus also has extensive capacity for regeneration, although this does decline during aging.

Recent studies in tissues such as liver, lung and bone marrow have revealed that ECs not only passively deliver oxygen and nutrients to tissues, but also actively produce distinct paracrine factors that can orchestrate their repair. The role of thymic ECs in thymopoiesis beyond their contribution of local circulation and the importation of lymphoid progenitors has not been comprehensively studied.

There have been several strategies proposed for boosting thymus regeneration and recent discoveries have revealed pathways underlying endogenous regeneration. Although it is clear endothelial cells play a role in tissue regeneration, this has traditionally been attributed towards their role in vascularization, including in the thymus where EC production of VEGF is important during regeneration.

Thus the need exists for strategies to promote immune function, and offer therapies to boost thymic function

SUMMARY OF THE DISCLOSURE

The present disclosure relates to methods and compositions for promoting thymic regeneration and enhancing thymic epithelial cell function following thymic injury or damage.

In one aspect, the present disclosure relates to a method to promote thymic regeneration following injury or damage to the thymus, the method comprising contacting the thymus with bone morphogenetic protein 4 (BMP4) in an amount sufficient to increase thymic cellularity and/or promote regeneration of the injured thymus. In some embodiments, the injured thymus is contacted with recombinant BMP4. In some embodiments, the injury or damage to the thymus is due to aging, stress, infection, cytoreductive chemotherapy, corticosteroids, or radiation.

In another aspect, the present disclosure relates to a method for enhancing thymic epithelial cell function in a thymus following injury or damage to the thymus, the method comprising introducing into the thymus thymic endothelial cells (ECs) that secrete BMP4 to increase the levels of BMP4 in the damaged thymus. In some embodiments, the enhancement of thymic epithelial cell function is characterized by an increased number of mature functional T-cells in the thymus.

In yet another aspect, the present disclosure relates to a method to promote thymic regeneration following injury or damage to the thymus, the method comprising introducing into the thymus thymic endothelial cells (ECs) that express and secrete BMP4. In some embodiments, the thymic endothelial cells are transduced with a viral gene, such as adenoviral gene E4ORF1. In some embodiments, the promotion of thymic regeneration is characterized by an increased number of mature functional T-cells in the thymus.

In another aspect, the present disclosure relates to a method to promote thymic regeneration following injury or damage to the thymus, wherein BMP4 or thymic endothelial cells that secrete BMP4 are applied to the thymus at 1 day pre-injury (for example, prior to radiation exposure) or from 1 to 5 days following damage or injury. In some embodiments, BMP4-producing thymic endothelial cells are administered intravenously; in some other embodiments, BMP4-producing thymic endothelial cells are administered intrathymically.

In yet another aspect, the present disclosure relates to a method for increasing thymic cellularity in a subject following injury or damage to the thymus, the method comprising administering to the subject an effective amount of ex vivo expanded thymic endothelial cells transduced to express and secrete BMP4. In some embodiments, the effective amount of BMP4-producing thymic endothelial cells is a dose of between $5 \times 10^3$ to $1 \times 10^7$ cells; in one embodiment between $1 \times 10^4$ and $1 \times 10^6$ cells; and in yet another embodiment, between $5 \times 10^4$ and $5 \times 10^5$ cells.

In one aspect, the present disclosure relates to a method to promote thymic regeneration in a subject following injury or damage to the thymus, the method comprising administering a therapeutically effective amount of bone morphogenetic protein 4 (BMP4) to the subject. In some embodiments, BMP4 is recombinant BMP4. In some embodiments, the injury or damage to the thymus is due to aging, stress, infection, cytoreductive chemotherapy, corticosteroids, or radiation.

In another aspect, the present disclosure relates to a method for enhancing thymic epithelial cell function in a subject following injury or damage to the thymus, the method comprising transplanting thymic endothelial cells (ECs) to the subject to increase the levels of BMP4 in the thymus.

In yet another aspect, the present disclosure relates to a method to promote thymic regeneration in a subject following injury or damage to the thymus, the method comprising administering to the subject thymic endothelial cells (ECs)

that express and secrete BMP4. In some embodiments, the thymic endothelial cells are transduced with a viral gene, such as adenoviral gene E4ORF1. In some embodiments, the thymic endothelial cells transduced with E4ORF1 (exEC$^{E4ORF1}$) are derived from thymic tissue. In some embodiments, the injury or damage to the thymus is due to aging, stress, infection, cytoreductive chemotherapy, corticosteroids, or radiation.

In another aspect, the present disclosure relates to a method to promote thymic regeneration in a subject following injury or damage to the thymus, wherein exEC$^{E4ORF1}$ are administered to the subject 1 day pre-injury (for example, prior to radiation exposure) or from 1 to 5 days following damage or injury. In some embodiments, exEC$^{E4ORF1}$ are administered intravenously; in some other embodiments, exEC$^{E4ORF1}$ are administered intrathymically.

In yet another aspect, the present disclosure relates to a method for increasing thymic cellularity in a subject following injury or damage to the thymus, the method comprising administering to the subject an effective amount of ex vivo expanded thymic endothelial cells transduced with E4ORF1 (exEC$^{E4ORF1}$). In some embodiments, the effective amount of exEC$^{E4ORF1}$ is a dose of between $5\times10^3$ to $1\times10^7$ cells; in one embodiment between $1\times10^4$ and $1\times10^6$ cells; and in yet another embodiment, between $5\times10^4$ and $5\times10^5$ cells.

Figure 6:
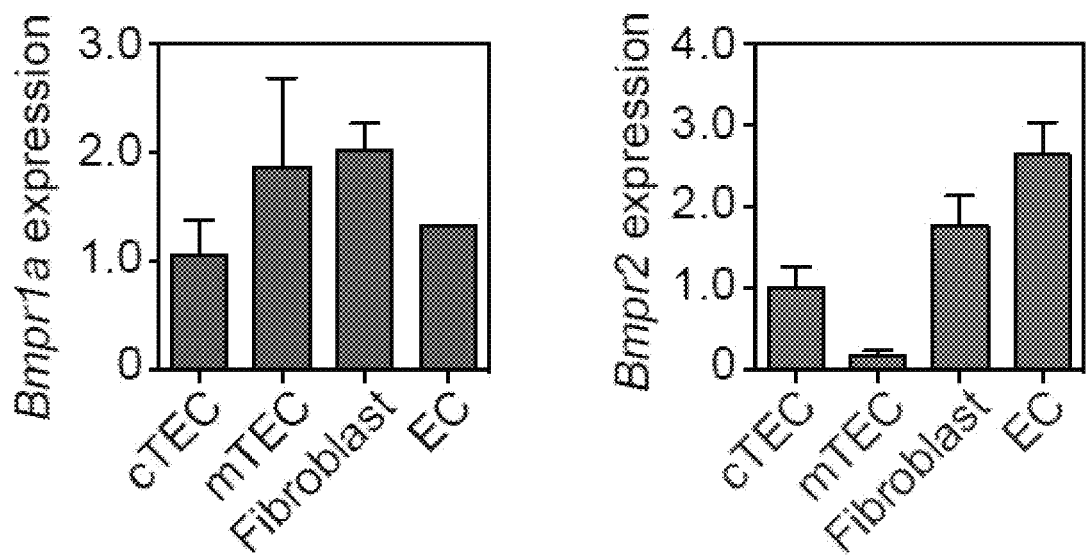

FIG. 6 shows that BMP receptors are expressed throughout the thymus on both developing thymocytes and the non-hematopoietic stromal compartment. Cell subsets of the thymus were FACS sorted and expression of Bmpr1a and Bmpr2 were assessed by qPCR. Cell populations analyzed in the thymus: cTEC (CD45−EpCAM+MHCII+UEA1$^{lo}$Ly51$^{hi}$); mTEC (CD45−EpCAM+MHCII+UEA1$^{hi}$Ly51$^{lo}$); Fibroblast (CD45−EpCAM−PDGFRα+); Endothelial cells (CD45−EpCAM−VE-cadherin+). Bar graphs represent mean±SEM of at least 2 independent experiments.

Figures 7A, 7B:
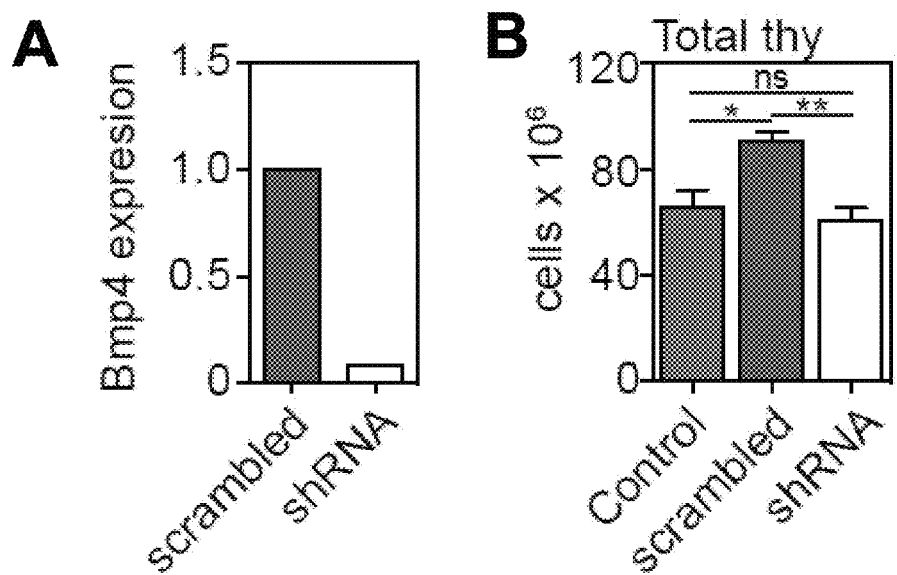
Figure 7C:
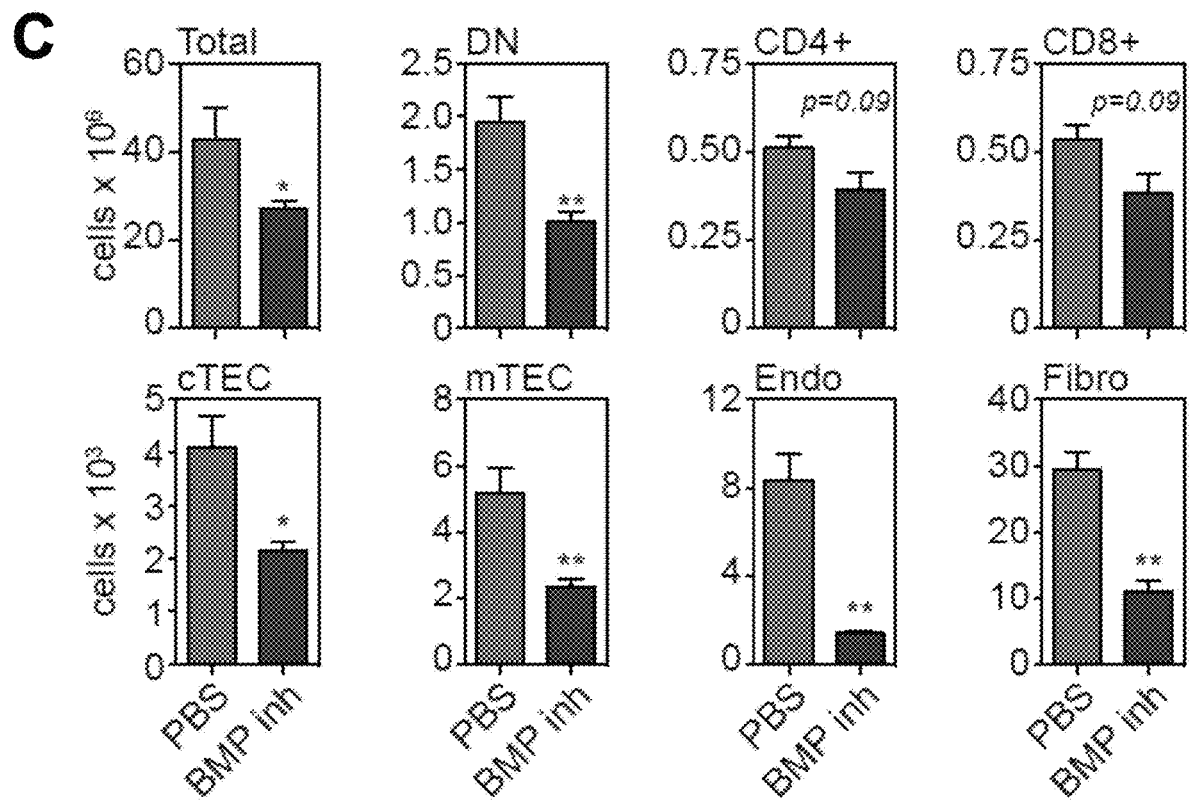

FIGS. 7A-7C shows that BMP4 produced by thymic ECs represents a non-redundant angiocrine factor mediating endogenous and exogenous thymic regeneration. exEC$^{E4ORF1}$ were generated from thymus ECs and transduced to express either a BMP4 shRNA or scrambled (non-functional) control and transferred into 6 week old (wo) C57BL/6 mice 3 days after SL-TBI. (A) BMP4 expression measured by qPCR. (B) Total thymus cellularity at day 9. (C) 6 week old C57BL/6 mice were administered with the BMP type I receptor inhibitor Dorsomorphin dihydrochloride (12.5 µg/g) i.p. at day −1 before SL-TBI (550cGy single dose) and twice daily after SL-TBI. Thymus was harvested at day 7 after TBI. Bar graphs represent mean±SEM of at least 2 independent experiments. *, $p<0.05$; , $p<0.01$, *, $p<0.001$.

Figure 8A:
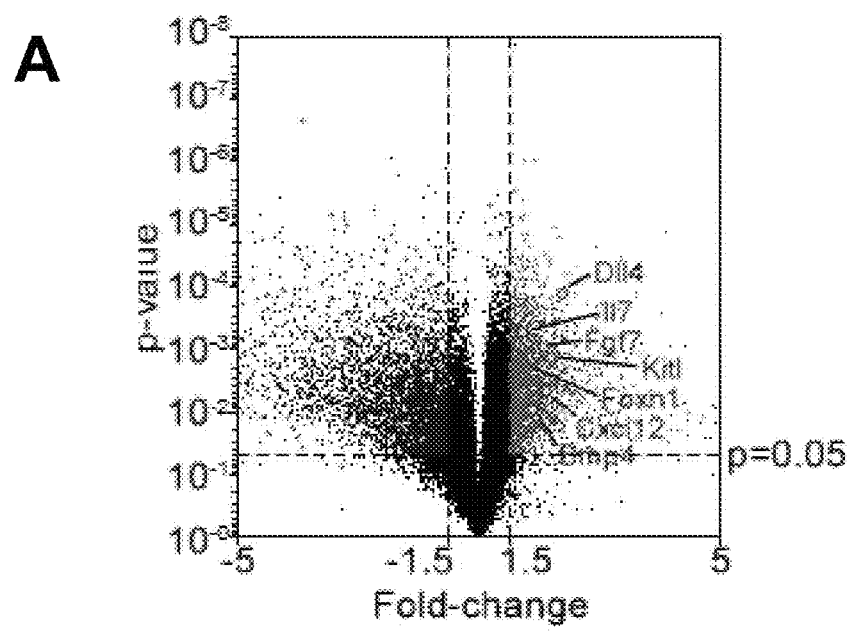
Figure 8B:
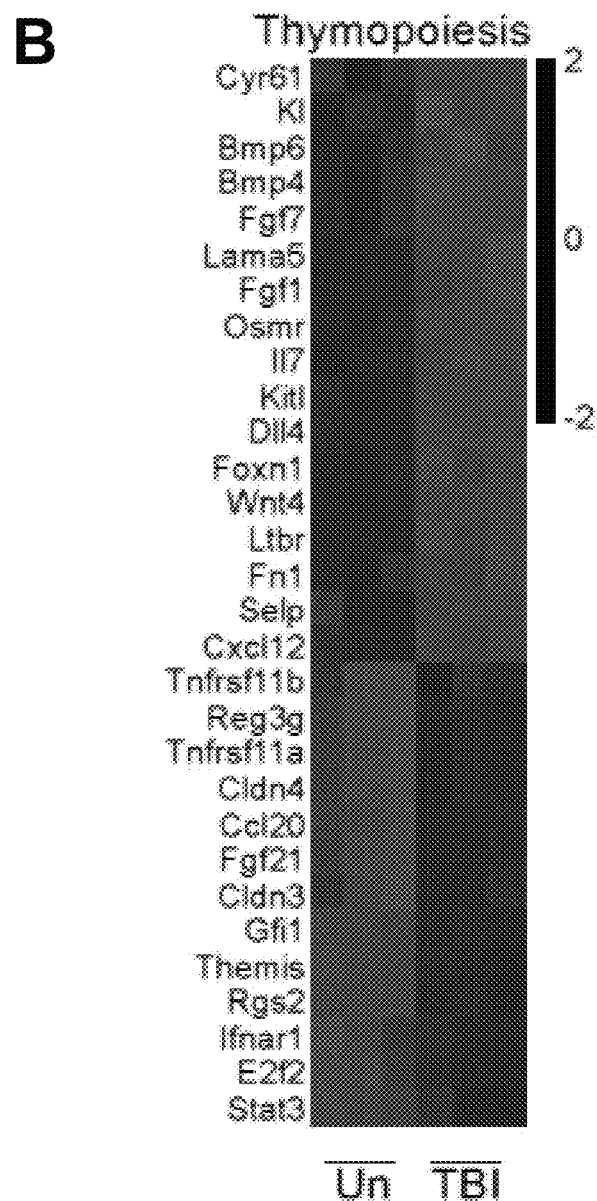
Figure 8C:
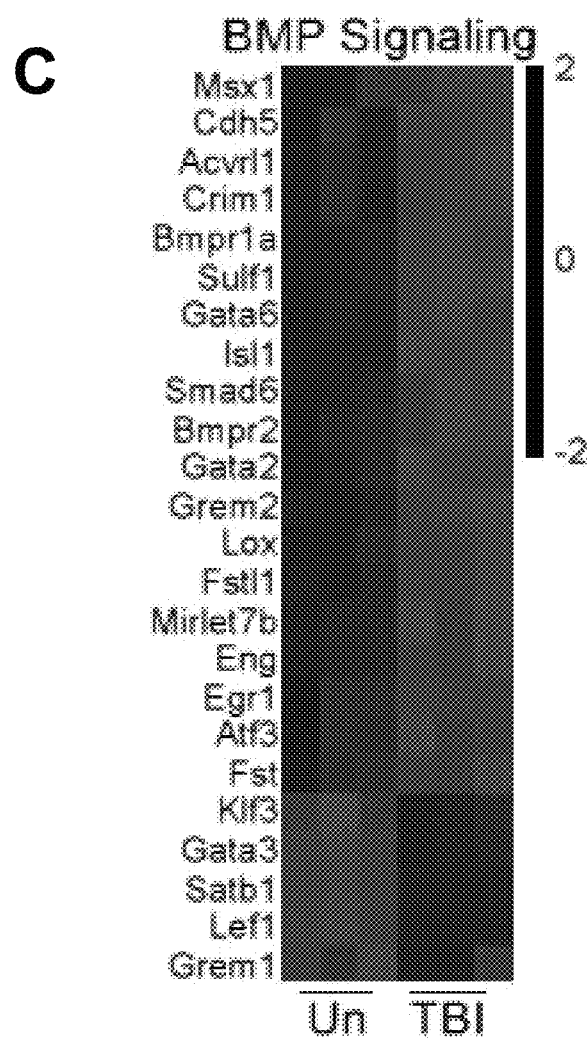
Figure 9A:
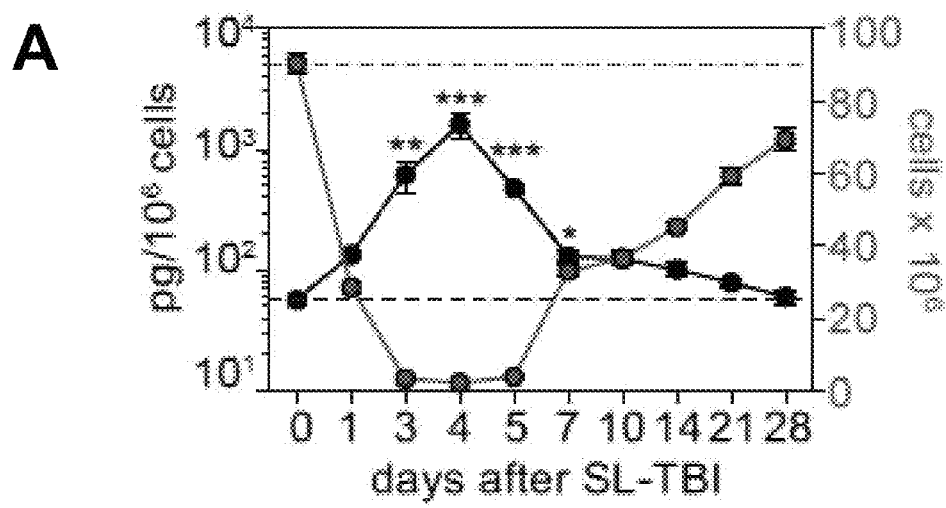
Figure 9B:
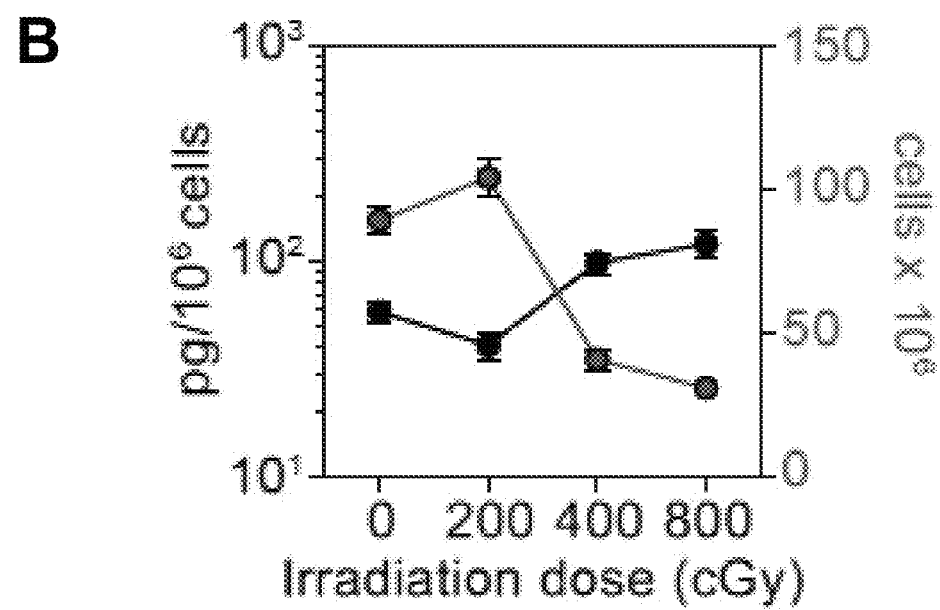
Figure 9C:
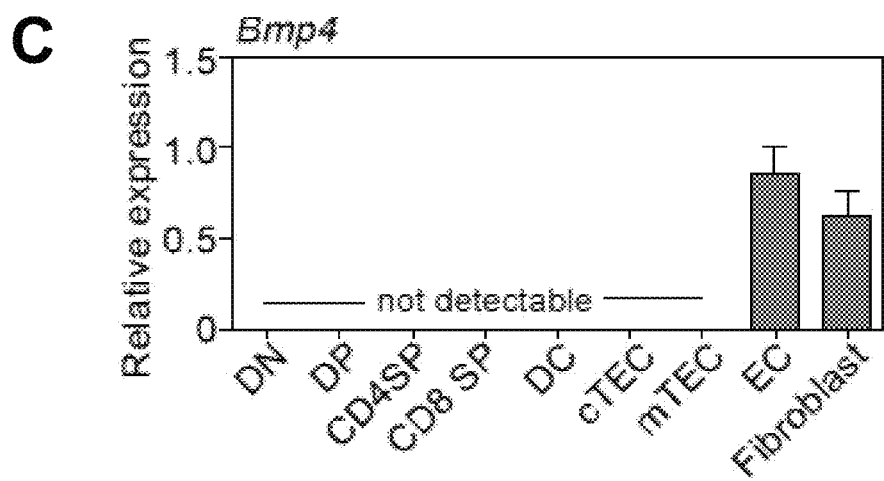
Figure 9D:
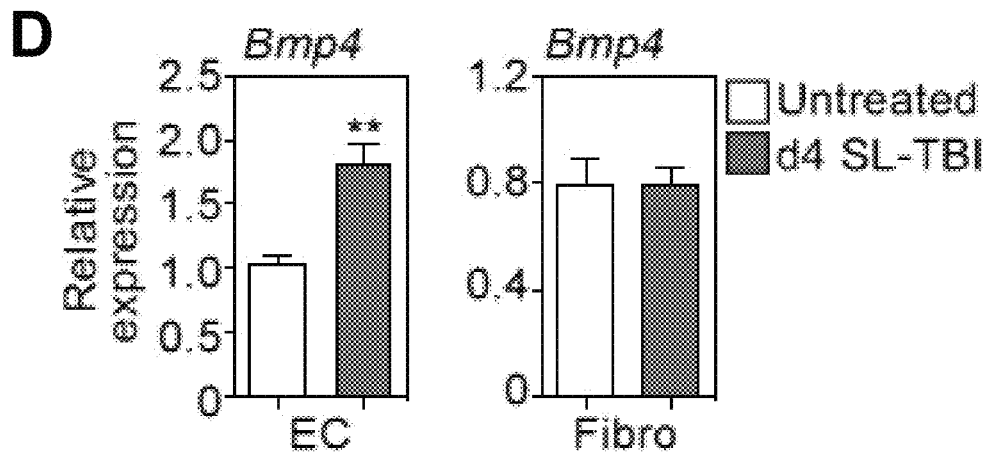

FIGS. 8A-8C Microarray analysis was performed on CD45− cells enriched from thymuses harvested from 6 week old C57BL/6 mice at days 0 and 7 after sublethal TBI (550 cGY). (A) Volcano plot outlining genes changed >1.5 fold, $p<0.05$ with some key thymus-related genes highlighted. (B) Heat map of thymus-specific genes changed >1.5 fold, $p<0.05$ after TBI. (C) Genes involved with BMP signaling that were changed >1.5 fold, $p<0.05$ after TBI. Bar graphs represent mean±SEM of at least 2 independent experiments. *, $p<0.05$; , $p<0.01$, *, $p<0.001$.

FIGS. 9A-9D (A) Graph of total thymus cellularity (right axis) and BMP4 measured by ELISA at multiple timepoints after SL-TBI. (B) Levels of BMP4 after targeted irradiation of the mediastinum. (C) Cell subsets comprising approximately 99% of the known cellular subsets in the thymus were FACS purified and assessed for their expression of Bmp4 at steady-state by qPCR. DN (CD4−CD8−), DP (CD4+CD8+), SP4 (CD4+CD8−CD3+), SP8 (CD4−CD8+CD3+), DC (CD11c+MHCII+), cTEC (CD45−EpCAM+MHCII+Ly51+UEA1$^{lo}$), mTEC (CD45−EpCAM+MHCII+Ly51$^{lo}$UEA1+), Fibroblasts (CD45−EpCAM−PDGFRα+), ECs (CD45−EpCAM−VE-Cad+). (D) ECs and Fibroblasts were FACS sorted at day 0 and 4 after SL-TBI and expression of Bmp4 was assessed by qPCR. Bar graphs represent mean±SEM of at least 2 independent experiments. *, $p<0.05$; , $p<0.01$, *, $p<0.001$.

Figure 10A:
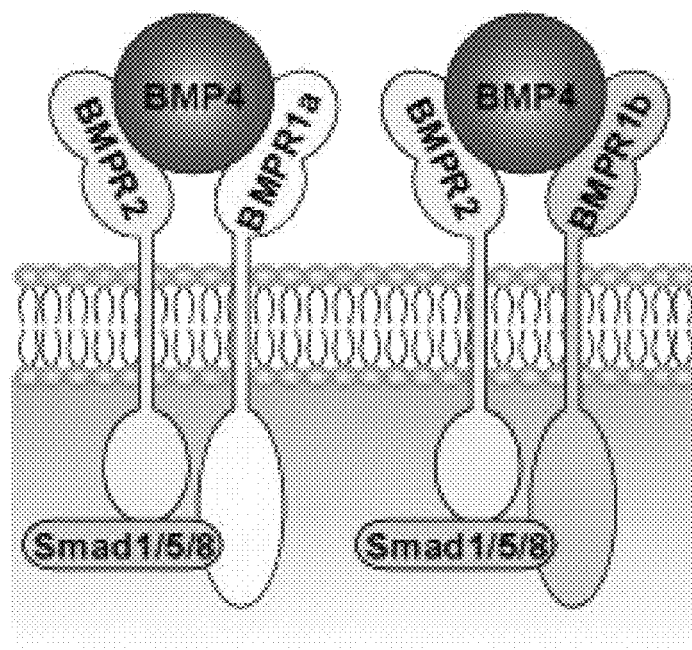
Figure 10B:
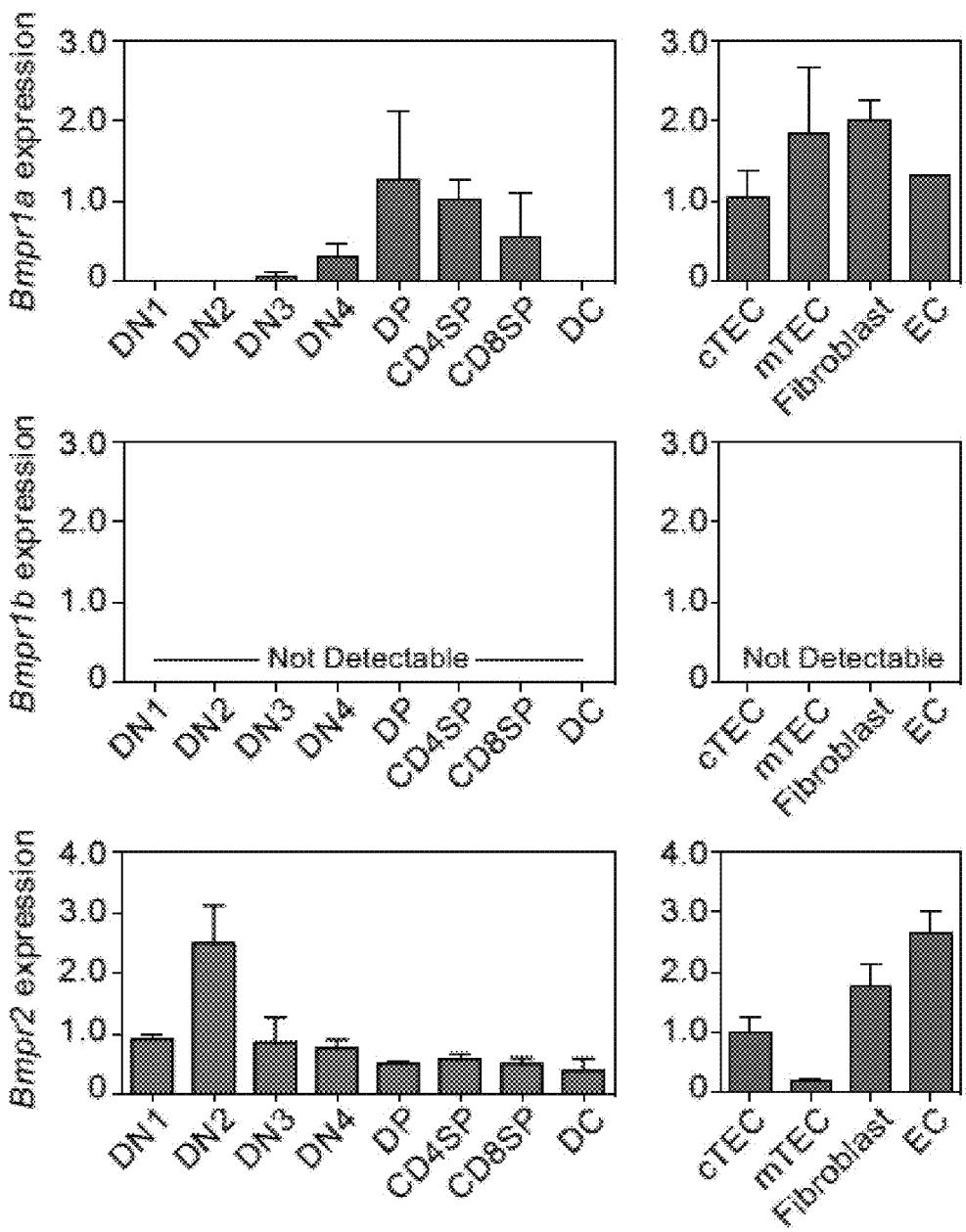
Figure 10C:
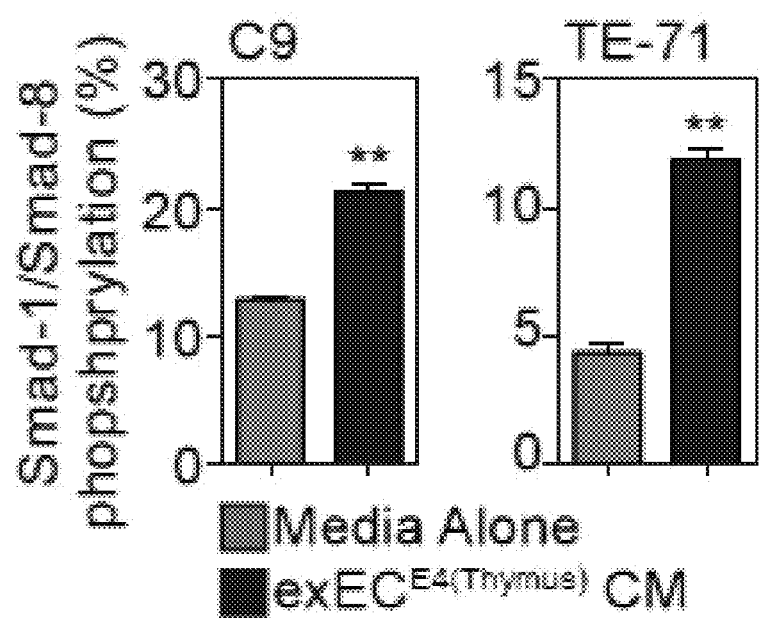
Figures 11A, 11B:
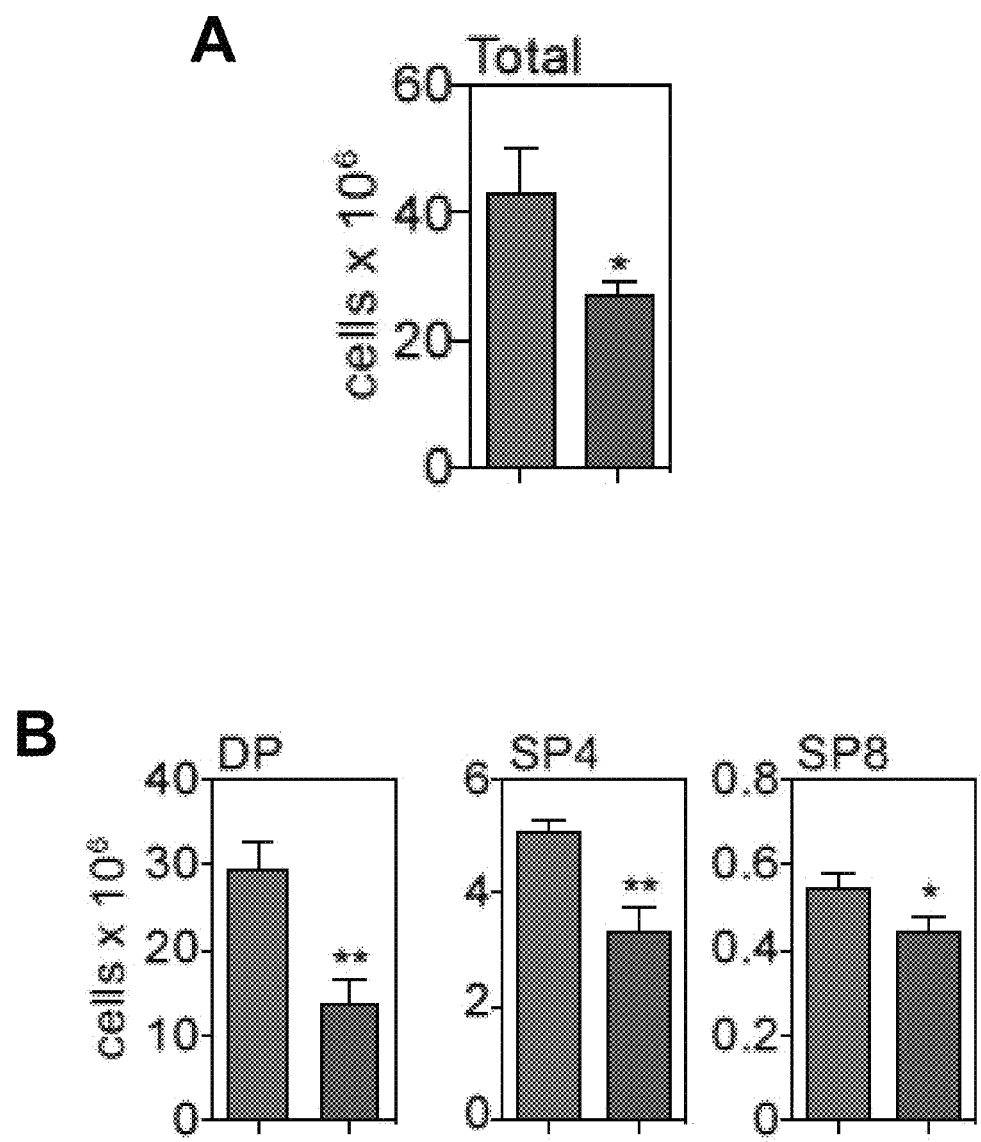
Figure 11C:
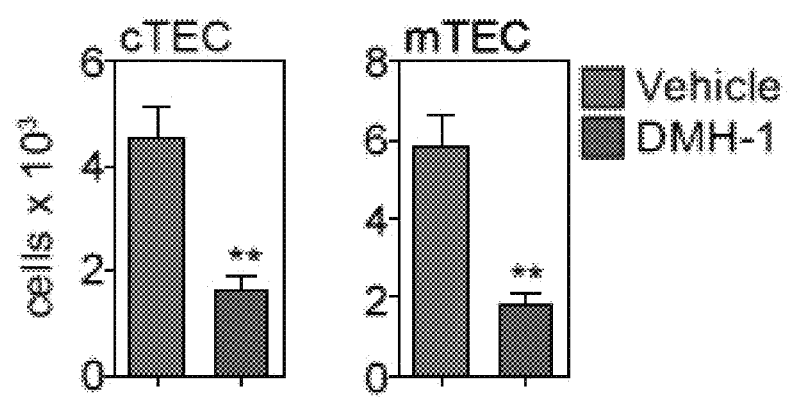
Figure 11D:
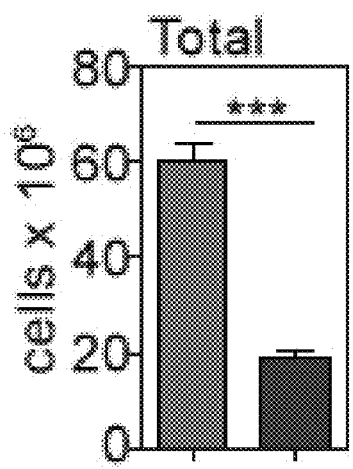
Figures 11E, 11F:
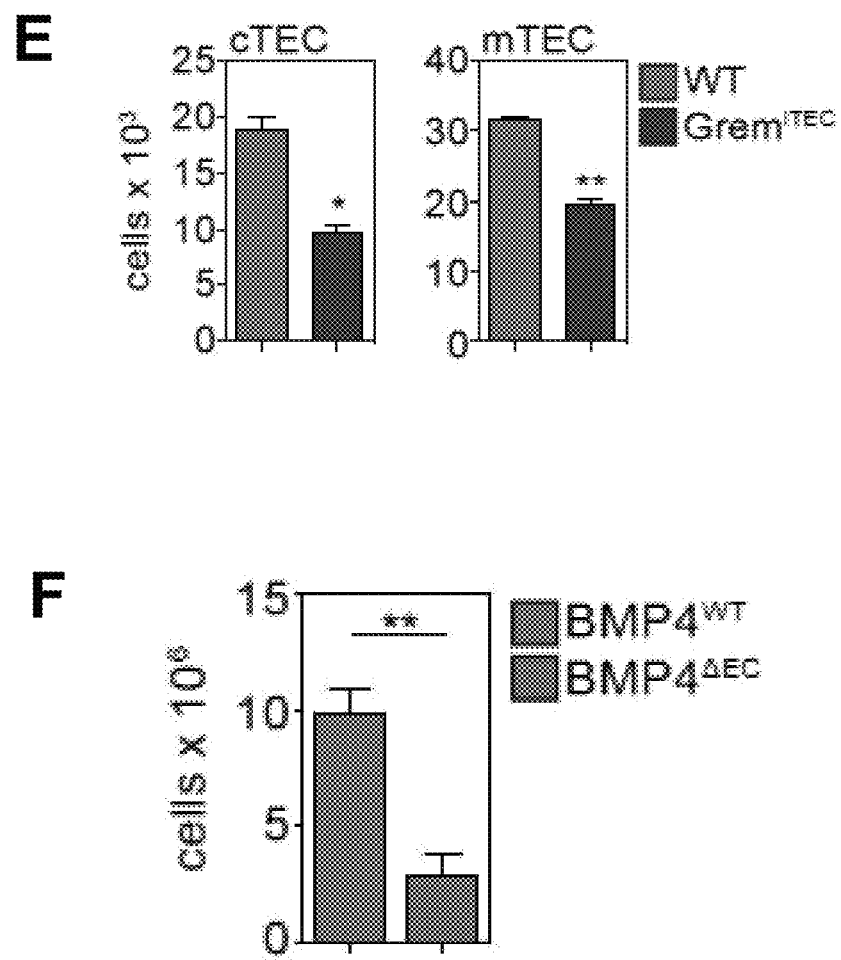
Figure 12A:
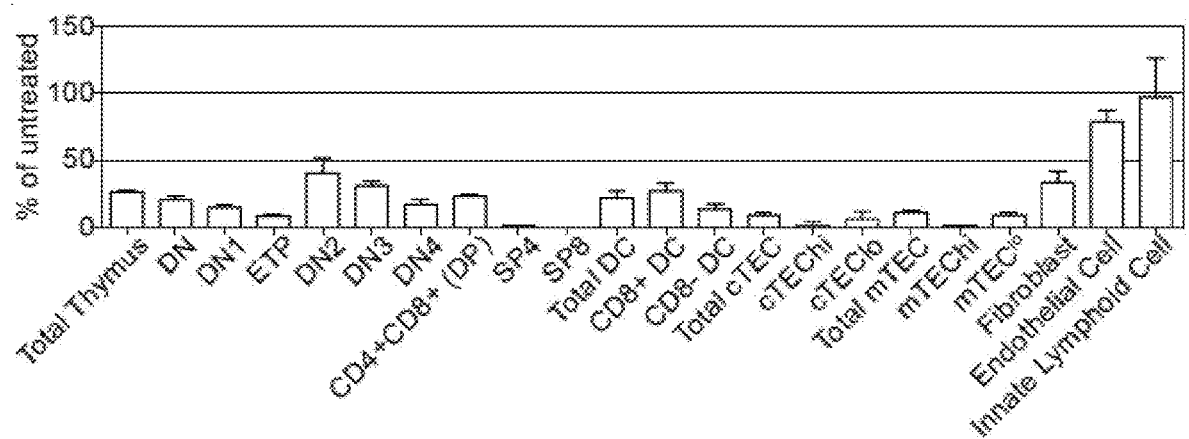
Figure 12B:
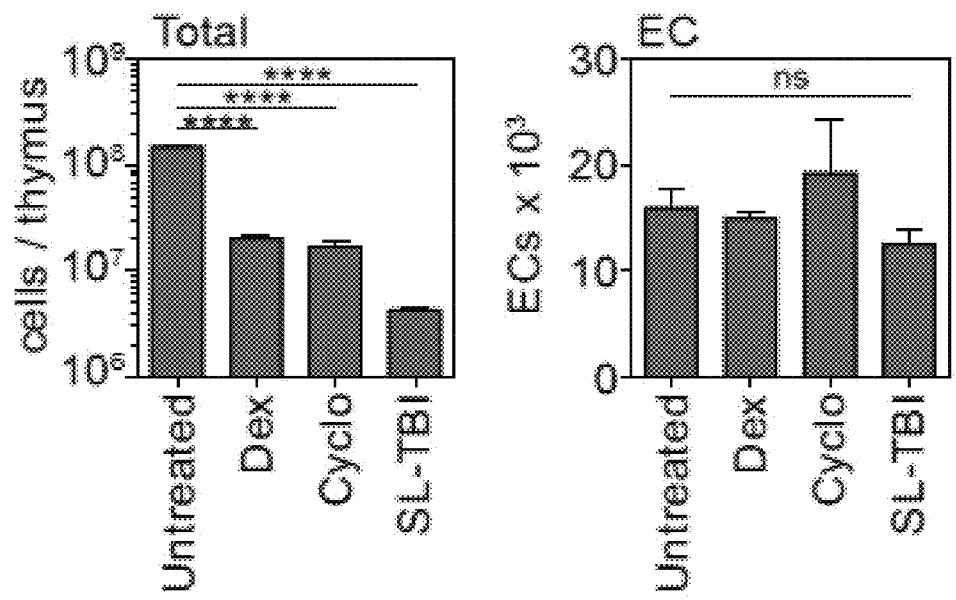
Figure 12C:
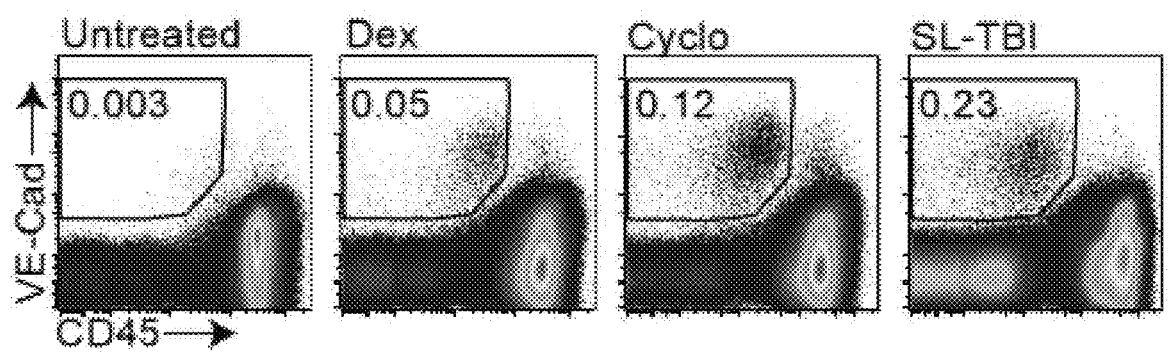
Figure 12D:
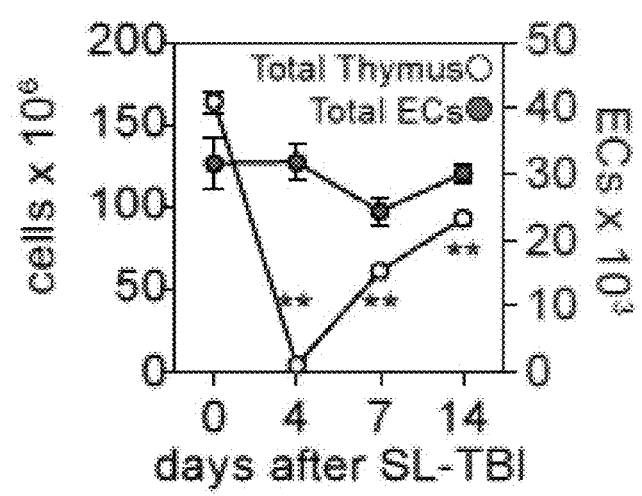
Figure 12E:
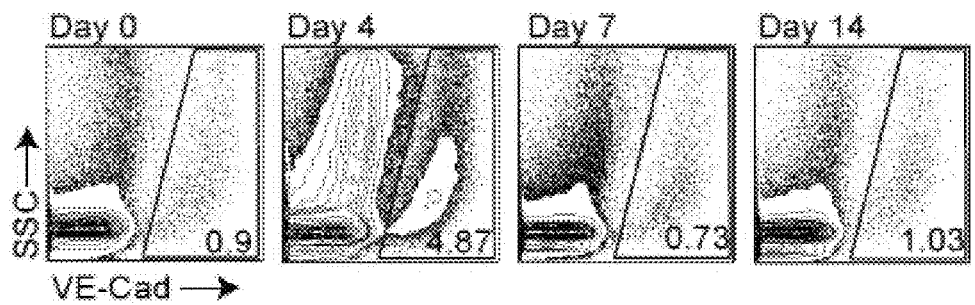
Figure 12E:
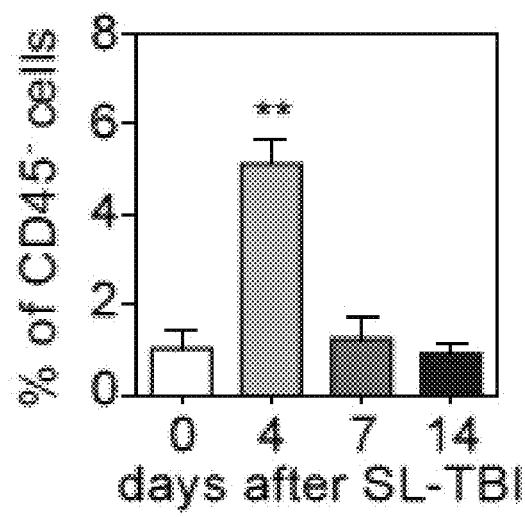
Figure 13A:
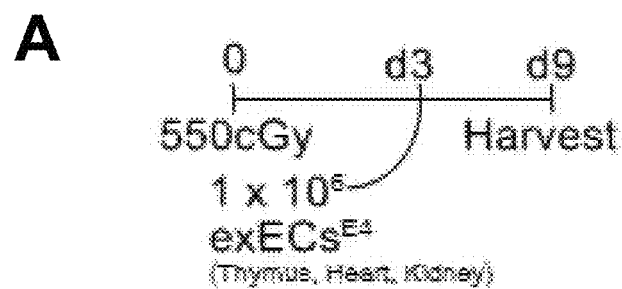
Figure 13B:
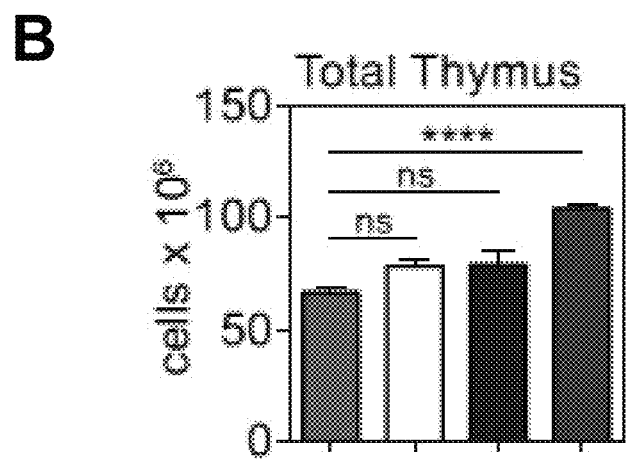
Figure 13C:
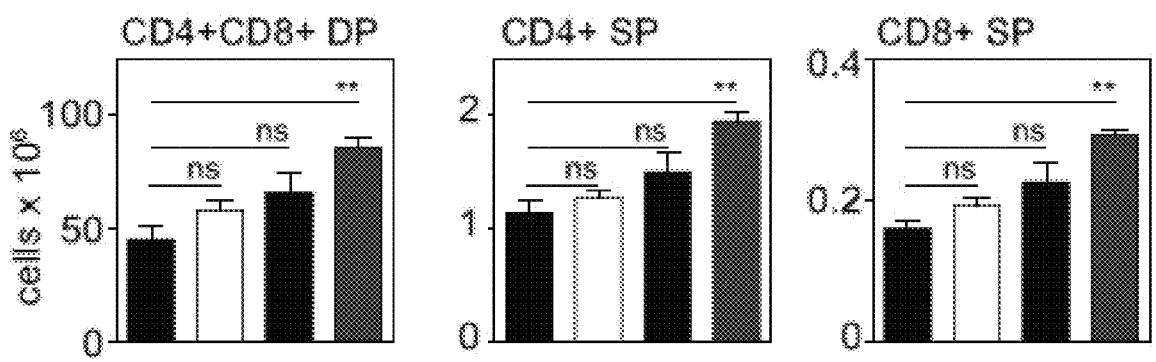
Figure 13D:
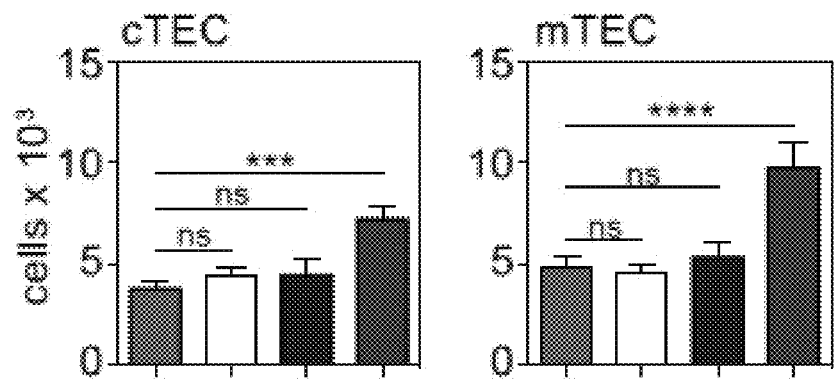
Figure 13E:
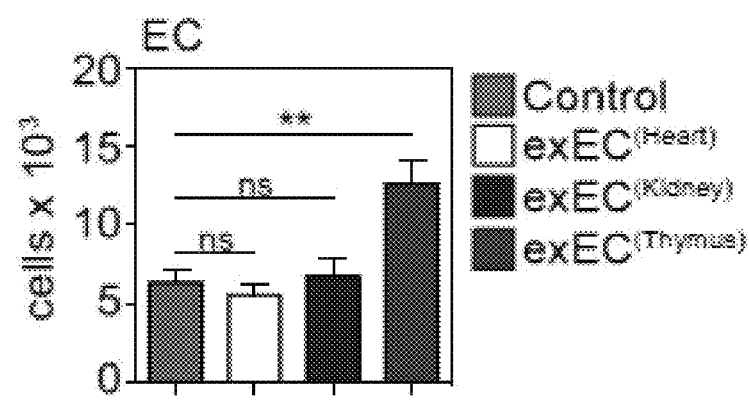
Figure 13F:
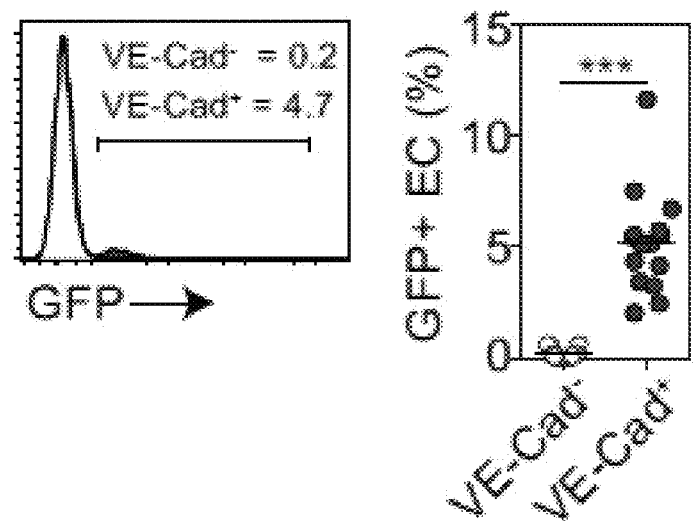
Figure 13G:
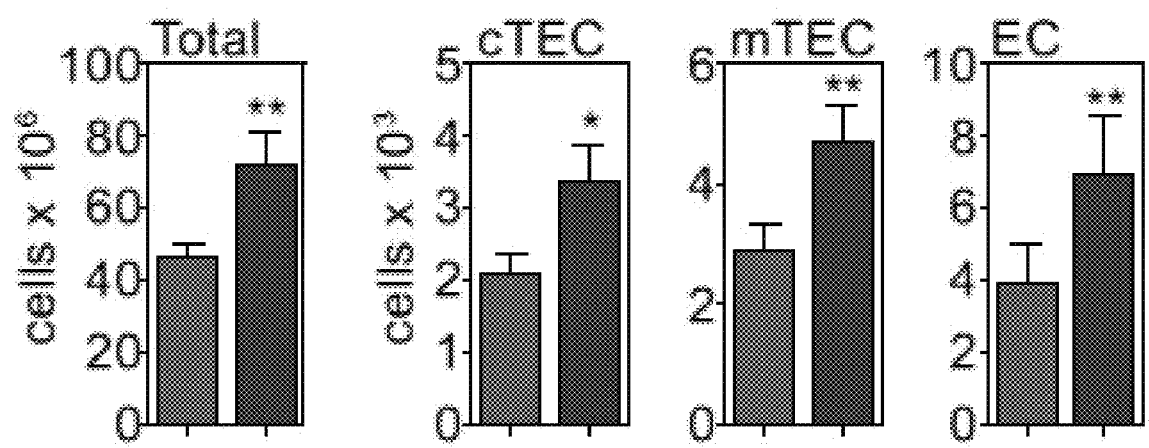
Figures 14A, 14B:
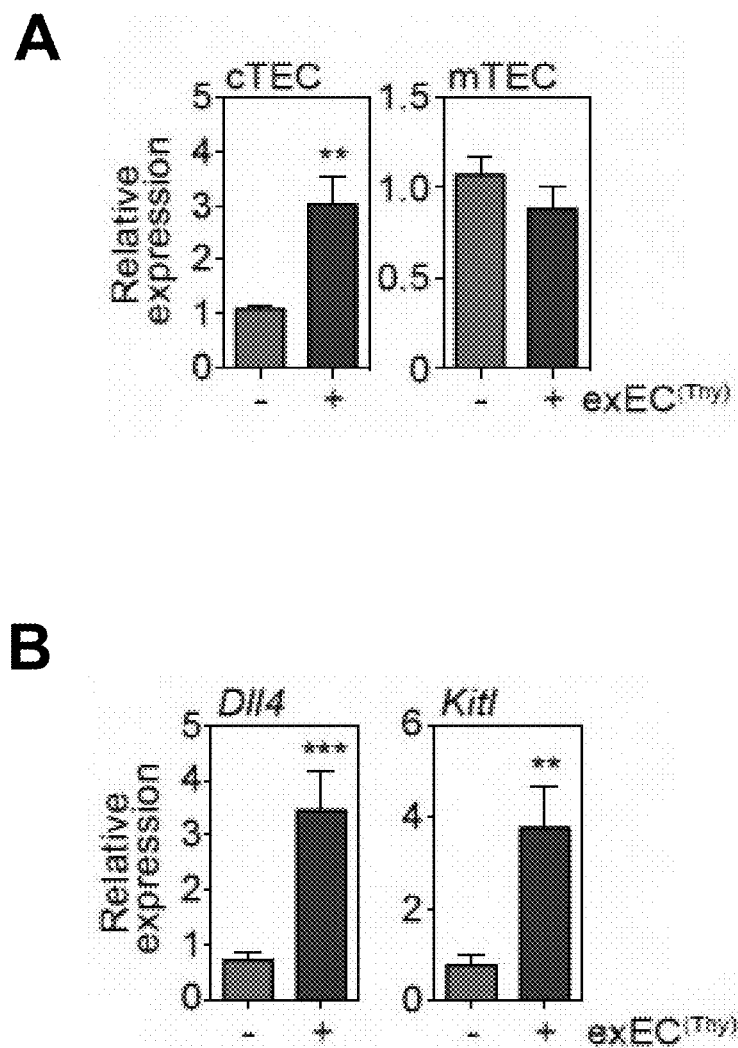
Figure 14C:
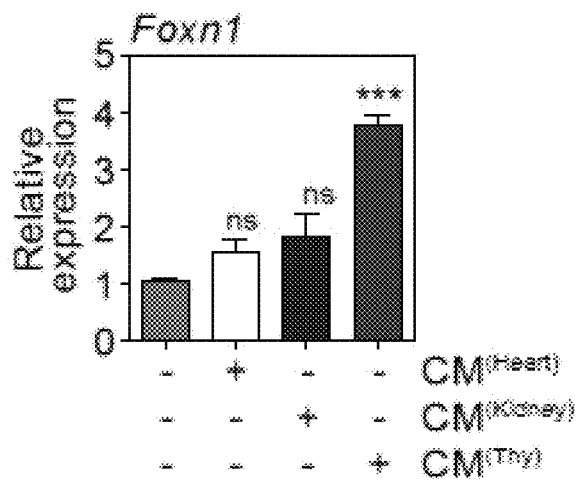
Figure 14D:
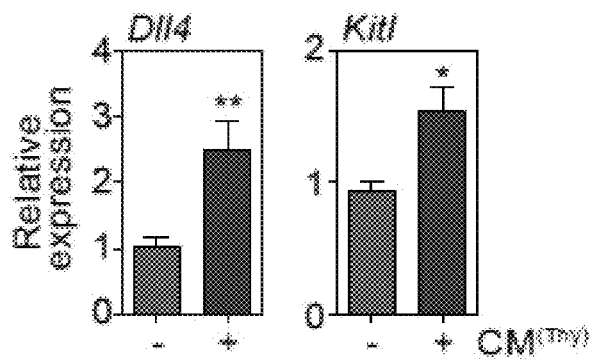

FIGS. 10A-10C (A) Receptor for BMP4 is comprised of a non-redundant Bmpr2 subunit, which pairs with either the Bmpr1a or Bmpr1b subunits. (B) Cell subsets comprising approximately 99% of the known cellular subsets in the thymus were FACS purified and assessed for their expression of Bmpr1a, Bmpr1b, and Bmpr2 at steady-state by qPCR. (C) C9 or TE-71 cell lines (cTEC or mTEC cell lines, respectively) were incubated with CM from exEC derived from thymus and downstream Smad-1/8 phosphorylation was assessed by flow cytometry after 20 minutes. Bar graphs represent mean±SEM. *, $p<0.05$; , $p<0.01$, *, $p<0.001$.

FIGS. 11A-11F (A-C) 6 week old C57BL/6 mice were administered with the BMP type I receptor inhibitor Dorsomorphin dihydrochloride (DMH-1, 12.5 µg/g) i.p. at day −1 before SL-TBI (550cGy single dose) and twice daily after SL-TBI. Thymus was harvested at day 7 after SL-TBI. (A) Total thymus cellularity, (B) numbers of thymocytes subsets, and (C) numbers of cTECs and mTECs. (D-E) A transgenic mouse with the BMP signaling inhibitor Gremlin-1 under the control of the ROSA26 locus were crossed with K5-CreER mice to create a tamoxifen inducible expression of Grem-1 in mTECs. (D) Total thymus cellularity. (E) Numbers of cTECs and mTECs. (F) BMP4$^{fl/fl}$ mice were crossed with VE-Cadherin-CreER mice and tamoxifen was administered on days −2, −1, 0, 1 and 2 surrounding SL-TBI (550cGy). Total thymus cellularity was assessed at day 7. Bar graphs represent mean±SEM of at least 2 independent experiments. *, $p<0.05$; , $p<0.01$, *, $p<0.001$.

FIGS. 12A-12E (A) Cell subsets in the thymus were assessed at day 7 after SL-TBI (550 cGy) and the depletion calculated compared to an untreated age-matched control cohort. Subsets analyzed include double negative (DN, CD4−CD8−) −1 (CD44+CD25−), ETP ((CD44+CD25−ckit+), DN2 ((CD44+CD25−), DN3 (CD44+CD25−), DN4 (CD44+CD25−), double positive (DP, CD4+CD8+), single positive (SP) −4 (CD3+CD8−CD4+), SP8 (CD3+CD4−CD8+), dendritic cells (DC, CD11c+MHCII+CD8+/−), cTEC (CD45−EpCAM+MHCII+Ly51+UEA1$^{lo}$), mTEC (CD45−EpCAM+MHCII+Ly51$^{lo}$UEA1+), fibroblast (CD45−EpCAM−MHCII−CD31−PDGFRα+), endothelial cells (CD45−EpCAM−MHCII−CD31+PDGFRα−), innate lymphoid cells (CD45+CD3−CD8−IL7Rα+CD4+RORγt+CCR6+). (B-C) 6 week old female C57BL/6 mice were treated with PBS (n=10), Dexamethasone (Dex, 50 mg/kg ip on day 0, n=10), cyclophosphamide (Cyclo, 100 mg/kg/day ip on days −1 and 0, n=10) or SL-TBI (550 cGy on day 0, n=10). On day 4, mice were perfused with 25 µg anti-VE-cadherin antibody (BV13) conjugated to Alexa 647 and then sacrificed and total thymic cellularity and endothelial cell number assessed. (B) Total cellularity and absolute number of endothelial cells in the thymus. (C) Concatenated flow cytometric plots detailing the proportion of CD45−VE-Cadherin+ cells in the thymus. (D-E), Female C57BL/6 mice were given SL-TBI (n=10-15/group) and assessed on days 4, 7 and 14. On the day of harvest mice were perfused with 25 µg anti-VE-cadherin antibody (BV13) conjugated to Alexa 647. (D) Total cellularity (open circles) and absolute number of endothelial cells (closed circles) in the thymus calculated using flow cytometry. (E) Proportion of VE-cadherin+ ECs as a function of CD45− stromal cells. Graphs represent mean±SEM of at least 2 independent experiments. *, $p<0.05$; , $p<0.01$, *, $p<0.001$.

FIGS. 13A-13G ECs were FACS sorted from the thymus, heart or kidney based on expression of VE-cadherin. Isolated cells were transduced with the viral gene E4ORF1. These cells are referred to as exEC. In order to model immune injury we exposed 6-8 weeks old C57BL/6 mice to a single dose of sublethal TBI (550cGy) and 1×10$^6$ exEC$^{E4}$ were administered intravenously at day 3 after SL-TBI (n=10-15/group). (A) Experiment schematic. (B) Total thymic cellularity at day 9 after SL-TBI. (C) Number of DP (CD4+CD8+), SP4 (CD4+CD3+) or SP8 (CD8+CD3+) Thymocytes. (D) Number of cortical and medullary thymic epithelial cells (cTEC and mTEC respectively). (E) Absolute number of ECs. (F-G) exEC$^{E4}$ were derived from mice with GFP under the control of a chicken β-actin promoter and transplanted into 6 week old mice 3 days after SL-TBI. (F) Thymus was harvested and GFP expression in thymic VE-Cadherin+ and VE-Cadherin– cells was assessed at day 9. (G) Total thymic cellularity and absolute number of cTEC, mTEC and ECs 28 days after SL-TBI and administration of $1 \times 10^6$ thymus-derived exEC$^{E4}$ on day 3. Graphs represent mean±SEM of at least 2 independent experiments. *, $p<0.05$; , $p<0.01$, *, $p<0.001$.

FIGS. 14A-14G (A-B) ECs were FACS sorted from the thymus based on expression of VE-cadherin and transduced with the viral gene E4ORF1. Thymus-derived exEC$^{E4}$ were transplanted intravenously into 6 week old C57BL/6 mice 3 days after SL-TBI. Thymus was harvested 4 days later and cortical and medullary TECs were FACS purified and expression of Foxn1 (A) or the Foxn1 downstream genes DII4, KitI and Cxcl12 (B) was measured by qPCR. (C-D) Conditioned media (CM) from in vitro cultures of exEC$^{E4}$ derived from thymus, heart or kidney were incubated with the cTEC cell line C9 for 24 hours when expression of Foxn1 (C) or the Foxn1 downstream genes DII4 or KitI (D) were assessed by qPCR. (E) Recombinant BMP4 (30 ng/ml) or CM from thymus-derived exEC$^{E4}$ was incubated with C9 cells for 24 hours when Foxn1 expression was assessed by qPCR. To inhibit BMP signaling, Noggin (100 ng/ml) was added to some wells. (F) exEC were generated from ECs derived from heart, kidney or thymus and expression of Bmp4 was measured by qPCR. (G) BMP4 protein was measured by ELISA in exEC cultures derived from thymus, heart or kidney. Graphs represent mean±SEM of at least 2 independent experiments. *, $p<0.05$; , $p<0.01$, *, $p<0.001$.

Figure 15A:
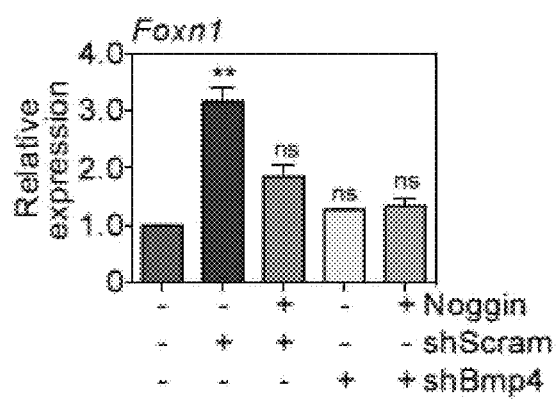
Figure 15B:
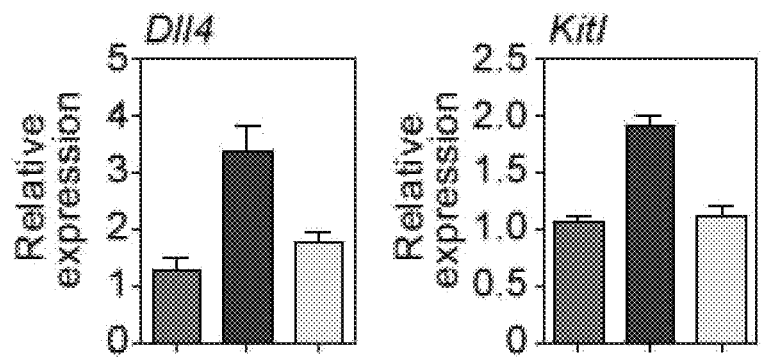
Figure 15C:
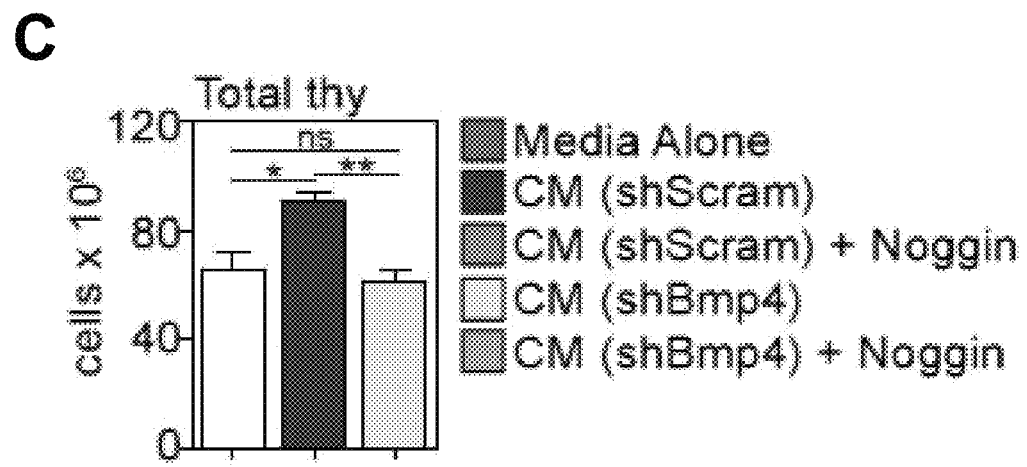

FIGS. 15A-15C exEC were generated from thymus-derived ECs and transduced to express either a Bmp4 shRNA (shBMP4) or scrambled (shScram) control. (A-B) CM derived from thymus shBMP4 or shScram exEC$^{E4}$ cultures was incubated with C9 cells for 24 hours when expression of Foxn1 (A) or the Foxn1 downstream genes DII4 and KitI was assessed by qPCR. (C) Total thymus cellularity at day 9 after shBmp4 or shScram were administered 3 days after SL-TBI. Bar graphs represent mean±SEM of at least 2 independent experiments. *, $p<0.05$; , $p<0.01$, *, $p<0.001$.

DETAILED DESCRIPTION

All patents, publications, applications and other references cited herein are hereby incorporated in their entirety into the present application.

In practicing the present invention, many conventional techniques in molecular biology, cell biology, biochemistry, and immunology are used, which are within the skill of the ordinary artisan. The contents of references containing standard protocols, widely known to and relied upon by those of skill in the art, including manufacturers' instructions are hereby incorporated by reference as part of the present disclosure.

In the description that follows, certain conventions will be followed as regards the usage of terminology. Generally, terms used herein are intended to be interpreted consistently with the meaning of those terms as they are known to those of skill in the art.

The term "thymic cellularity" refers to the state of a tissue, specifically thymus tissue as regards the number of its constituent cells.

The term "regeneration" refers to the process of renewal, restoration or growth that occurs in an organ or tissue that leads to replacement of constituent cells or tissue following loss due to injury or damage.

Continuous generation of adaptive immune diversity is dependent on T cell development in the thymus, which is extremely sensitive to damage caused by stress, infection, age, and cytoreductive treatments, such as chemotherapy and radiation therapy.

For patients whose thymus has been irrevocably damaged, or those patients whose thymic function has been compromised due to cytoreductive conditioning, infection, or age, therapeutic strategies to promote immune function and to boost thymic function would be greatly beneficial.

Kinetics of Thymic Regeneration

Figures 1A, 1B, 1C, 1D:
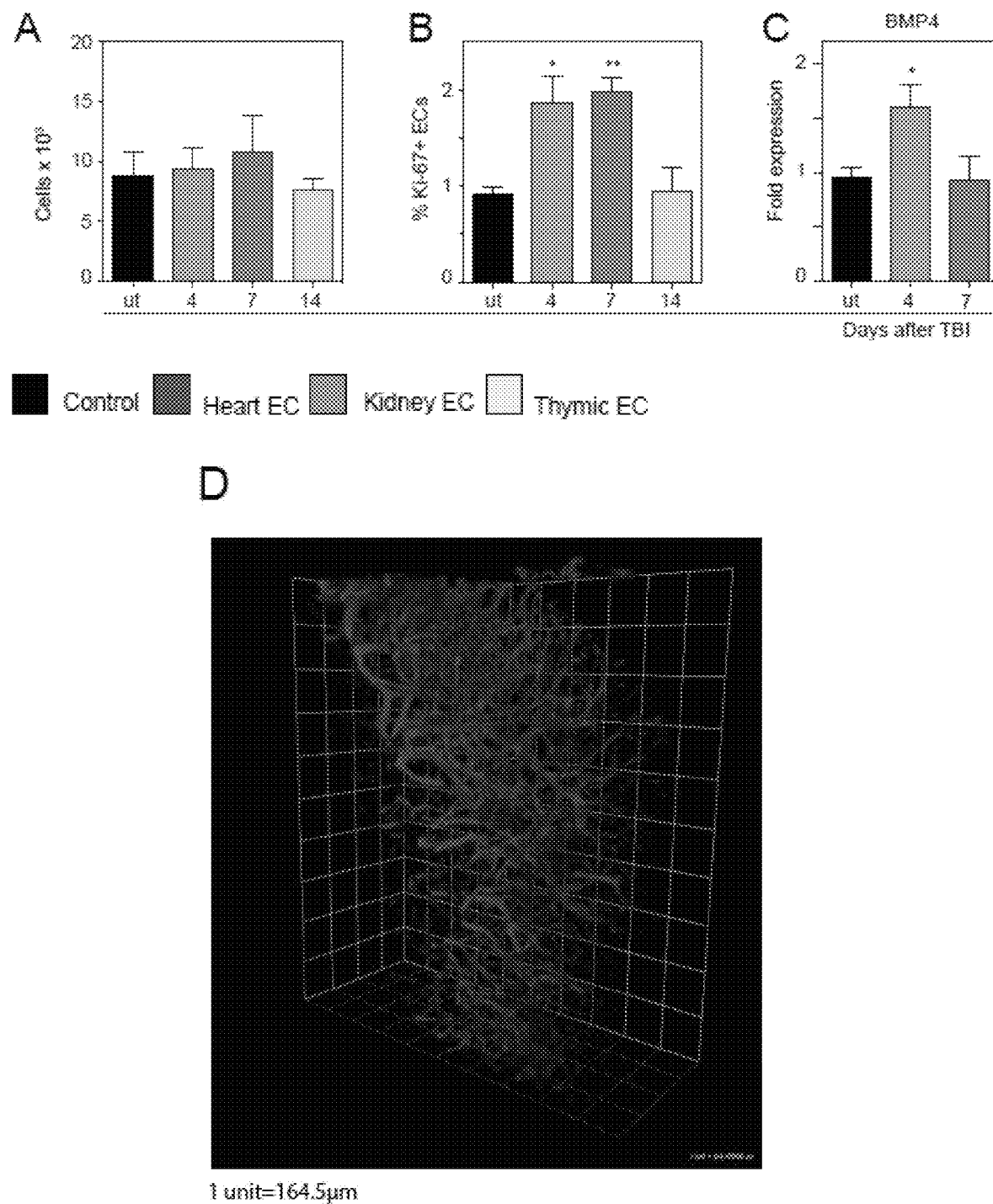
FIGS. 1A-1G show the kinetics of thymic recovery following total body irradiation (TBI, 550cGy) in young C57BL/6 mice. (A) Cellularity of thymic ECs of untreated (ut) mice and at different time points after TBI (550cGy). (B) Proliferation measured by Ki-67 expression with flow cytometry. (C) BMP4 mRNA expression of untreated (ut) at different timepoints after TBI (550cGy) measured by qPCR. (D) LSFM based 3D model of VE-Cadherin+ tECs in the thymus. (E) Total thymic cellularity of mice that were given a single dose of 550cGy and administered with DME, $10^6$ heart ex-EC, kidney ex-EC or thymic ex-EC. Thymuses were harvested at day 9 after TBI. (F) BMP4 mRNA expression of heart ex-EC, kidney ex-EC and thymic ex-EC measured by qPCR. (G) FOXN1 mRNA expression of TEC cell line C9+/−48 h EC conditioned medium+/−500 ng/ml recombinant Noggin, +/−30 ng/ml BMP4+/−500 ng/ml Noggin measured by qPCR compared to control, ˆ c.m.+ Noggin, # and BMP4.
Figures 1E, 1F, 1G:
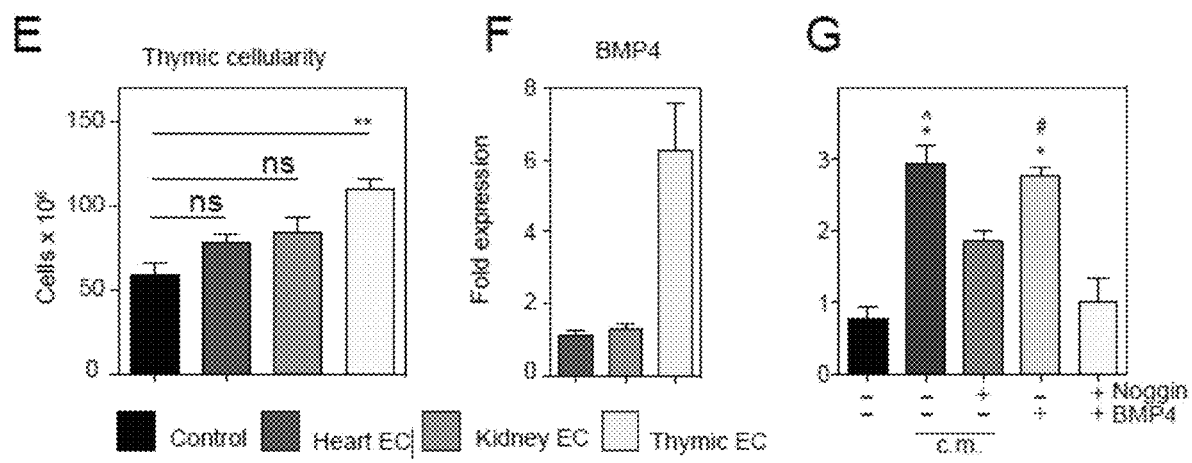
Figures 2A, 2B:
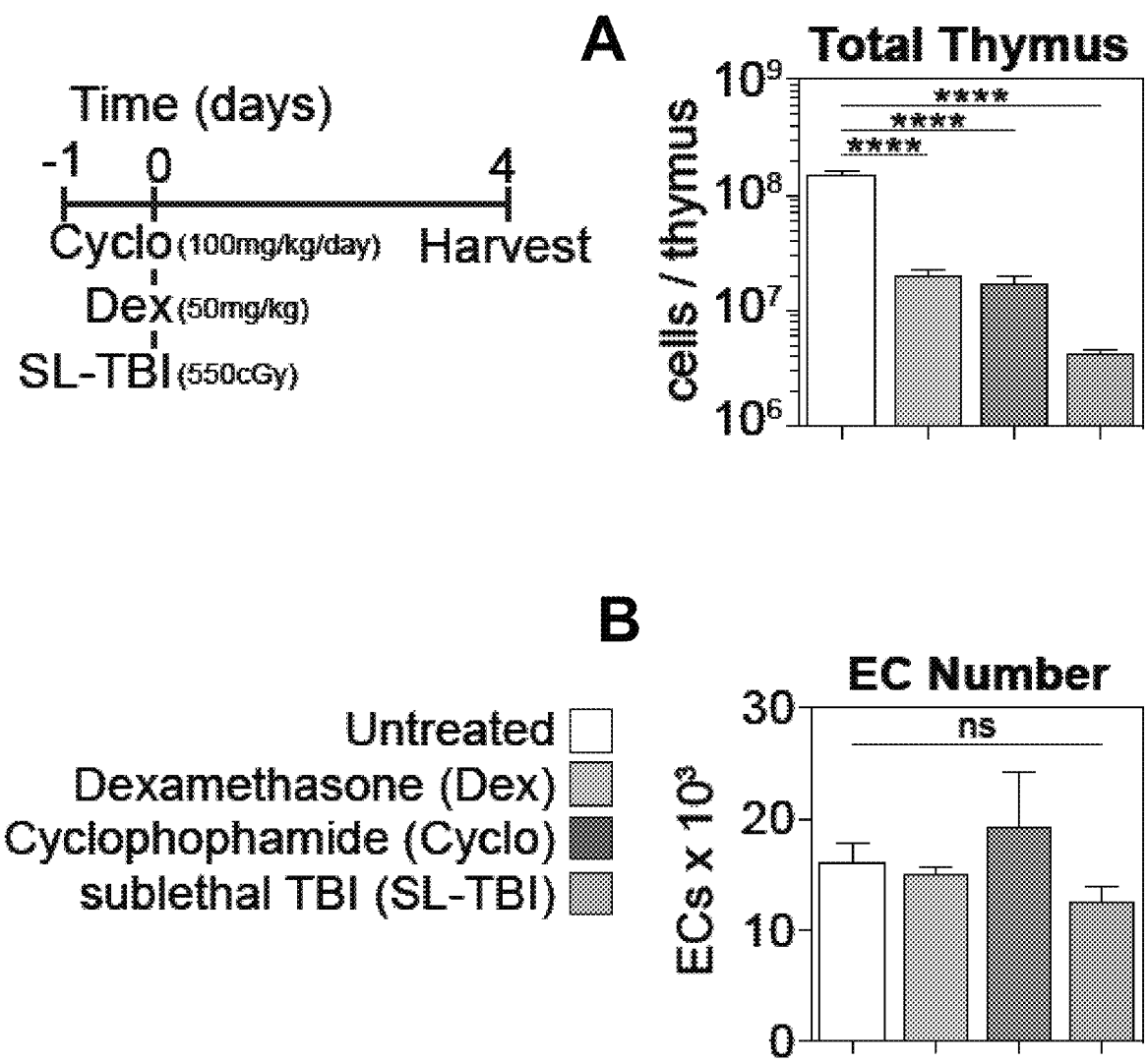
FIGS. 2A-2I show that endothelial cells represent a damage-resistant stromal population in the thymus. (A-C) 6 week old female C57BL/6 mice were treated with PBS (n=10), Dexamethasone (Dex, 50 mg/kg ip on day 0, n=10), cyclophosphamide (Cyclo, 100 mg/kg/day ip on days −1 and 0, n=10) or sublethal total body irradiation (SL-TBI, 550 cGy on day 0, n=10). On day 4, mice were perfused with 25 µg anti-VE-cadherin antibody (BV13) conjugated to Alexa 647 and then sacrificed and total thymic cellularity and endothelial cell number assessed. (A) Total thymic cellularity. (B) Proportion of CD45-VE-Cadherin+ cells in the thymus. (C) Total number of endothelial cells (ECs) in the thymus. (D-I) ECs were assessed at days 4, 7 and 14 of 6 week old female C57BL/6 mice treated with SL-TBI (n=10-15/group). On the day of harvest mice were perfused with 25 µg anti-VE-cadherin antibody (BV13) conjugated to Alexa 647. (D) Total thymic cellularity. (E) Total number of ECs. (F) Proportion of VE-cadherin+ ECs as a function of CD45− stromal cells. (G) Proportion of the thymus that are VE-cadherin+ ECs. (H) 3D reconstruction of whole thymus at timepoints after SL-TBI. Red color signifies staining with VE-cadherin antibody. (I) Proportion of Ki-67+ ECs after SL-TBI. Bar graphs represent mean±SEM of at least 2 independent experiments. *, $p<0.05$; , $p<0.01$; *, $p<0.001$.
Figure 2C:
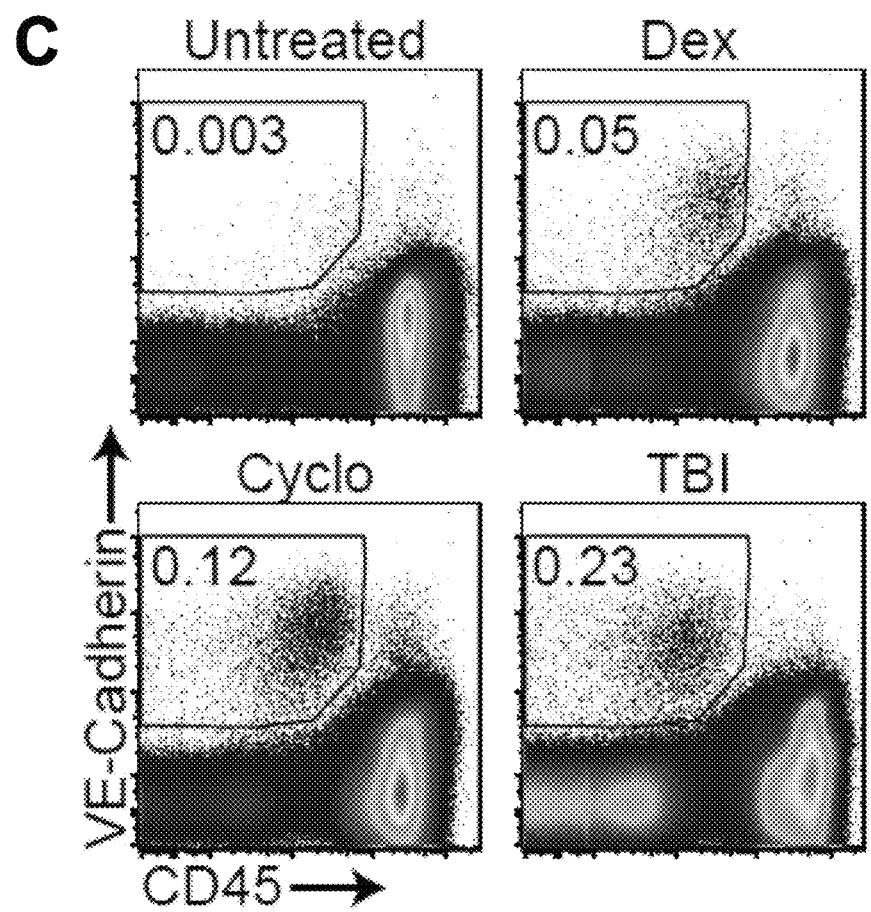

After damage to the thymus caused by cytoreductive chemotherapy, corticosteroids or total body irradiation (TBI), where total thymic cellularity has been entirely depleted (FIG. 2a), including subsets of thymocytes and thymic epithelial cells (TECs), the number of endothelial cells (ECs) remained unchanged (FIG. 2b).

Figures 2D, 2E, 2F:
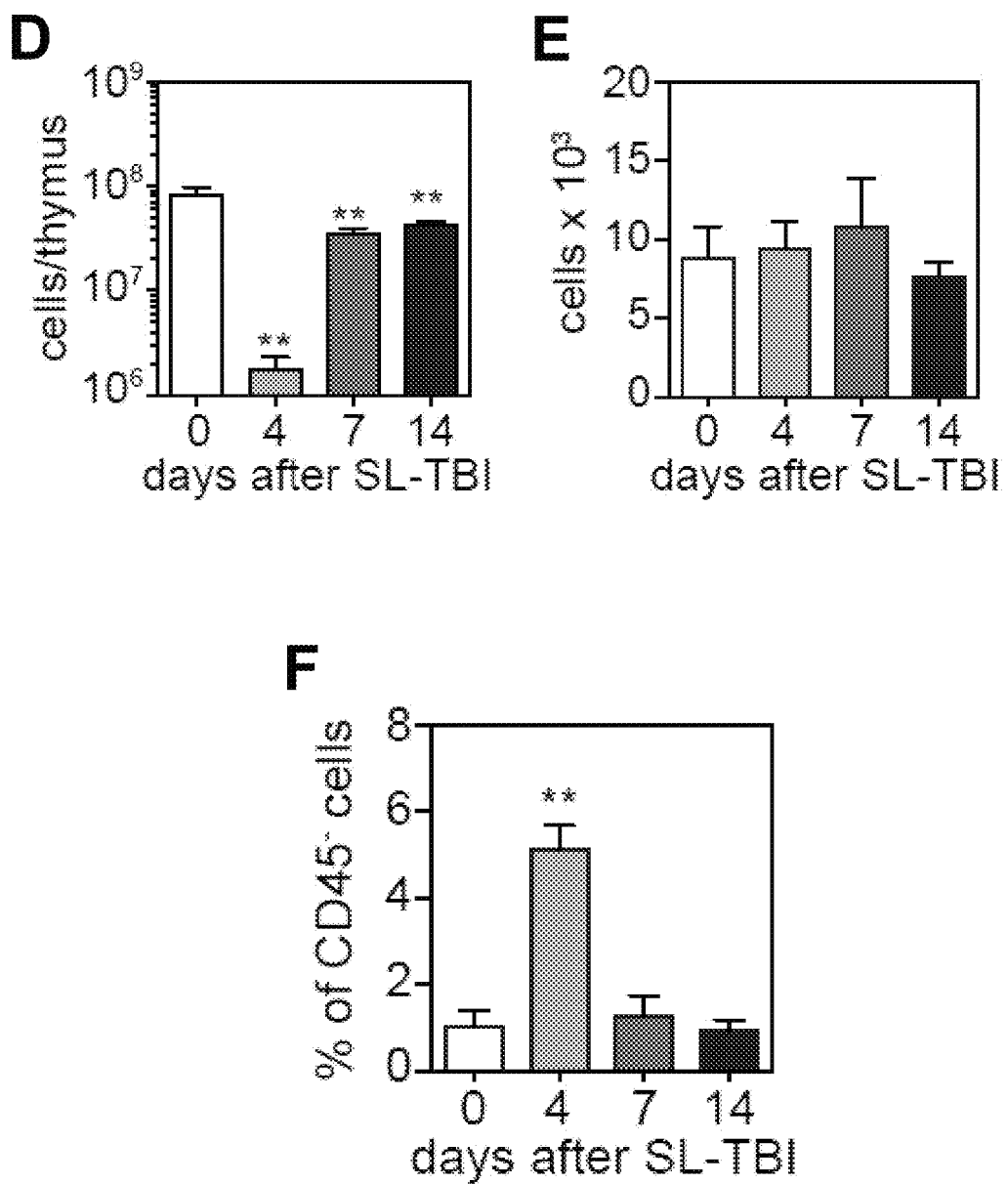
Figure 2G:
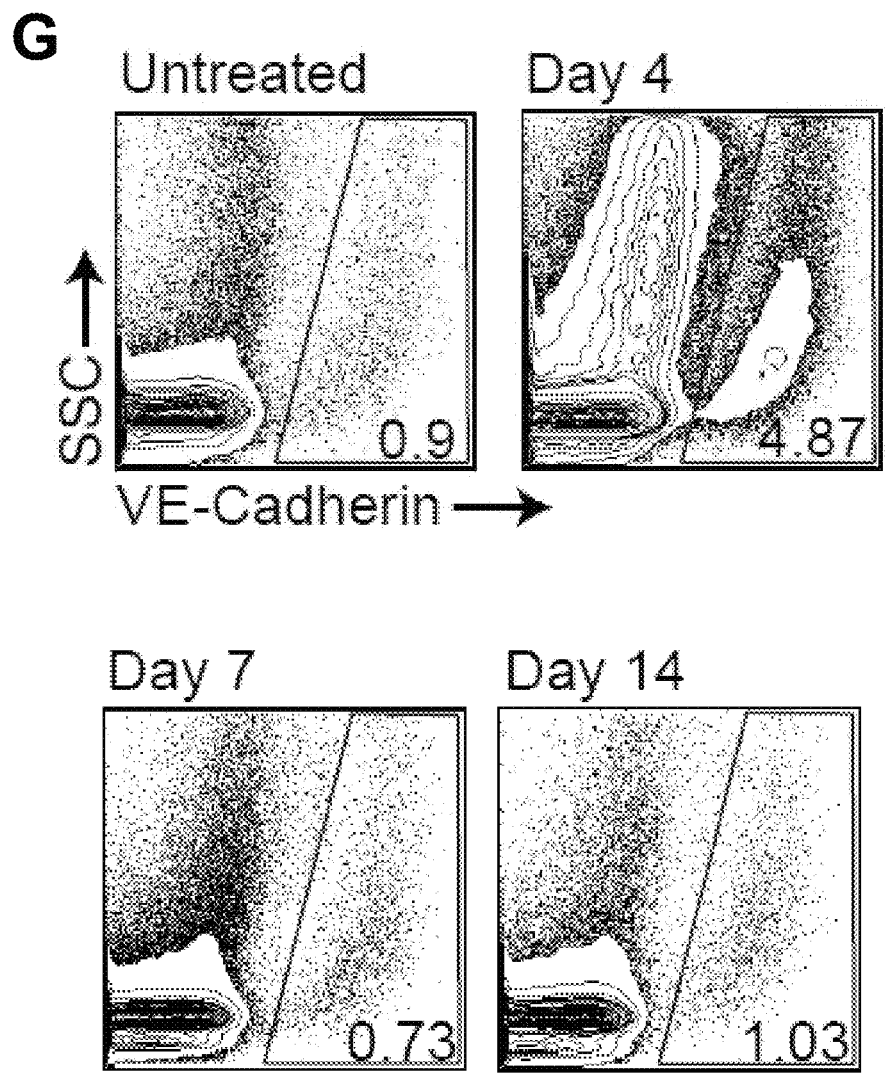
Figure 2H:
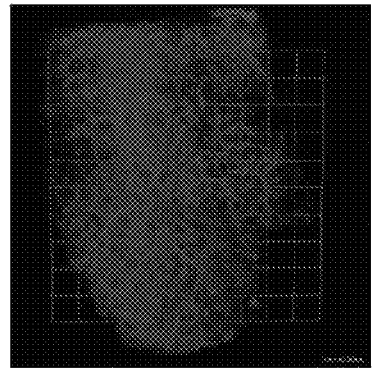
Figure 2H:
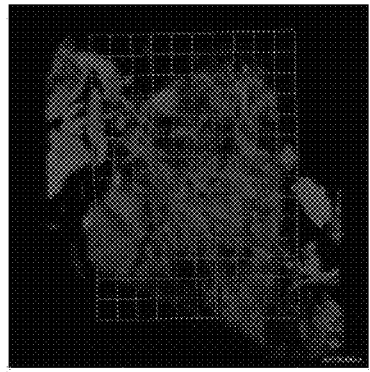
Figure 2H:
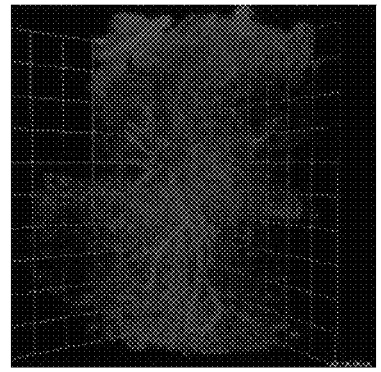
Figure 2H:
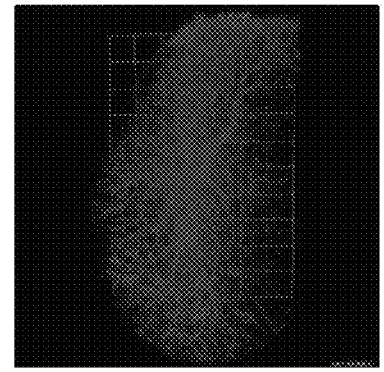
Figure 2I:
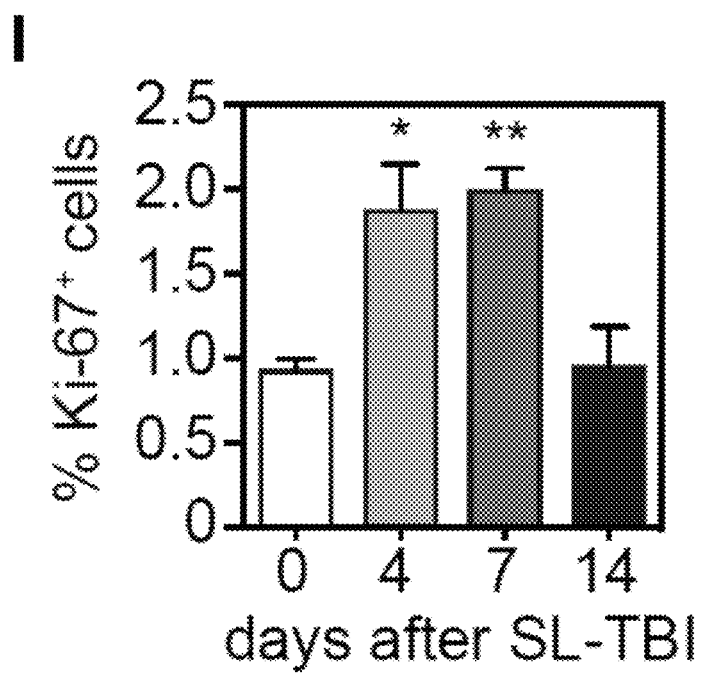

Starting with a model of thymic damage using sublethal TBI, it was observed that after an initial depletion of thymic cellularity at day 4, there is considerable recovery by day 7, and almost complete return to normal levels by day 14 (FIG. 2d). In contrast, the numbers of ECs remained unchanged through this kinetic analysis (FIG. 2e). Given the decrease in the number of other non-hematopoietic stromal cells, the proportion of CD45$^-$ cells actually increased early after damage (FIGS. 2f-g). However, although there is no change in the absolute number of ECs, the architecture of the thymus is disrupted leading to architectural changes and disruption in the thymus after TBI, such as reduced organ volume, and commensurate decrease in volume of vasculature (FIG. 2h).

Critical Role of Endothelial Cells in Thymic Recovery Following Injury or Damage.

Endothelial cells (ECs) play an active role in endogenous regeneration of the thymus and ECs play a critical role in aiding thymic recovery following injury or damage. The thymus may be injured or damaged from, for example, stress, infection, cytoreductive chemotherapy, corticosteroids, or radiation.

As demonstrated herein, ECs represent a highly damage-resistant niche in the thymus. Rather than being passive conduits that deliver oxygen and nutrients, ECs are active participants in organ function producing distinct paracrine factors that orchestrate repair of the thymus.

In one embodiment of the disclosed method for promoting thymic regeneration, exogenous thymic endothelial cells (exEC) are administered to a subject following injury or damage to the thymus. Methods for the isolation and enrichment of thymic endothelial cells are known in the art. exEC may be administered by any route known in the art that is suitable for the administration of cell-based therapies that provides a subject with a therapeutically effective dosage. In some embodiments, administration may be parenteral, for example, intravenous (iv) or intrathymic (it).

Figures 3A, 3B, 3C:
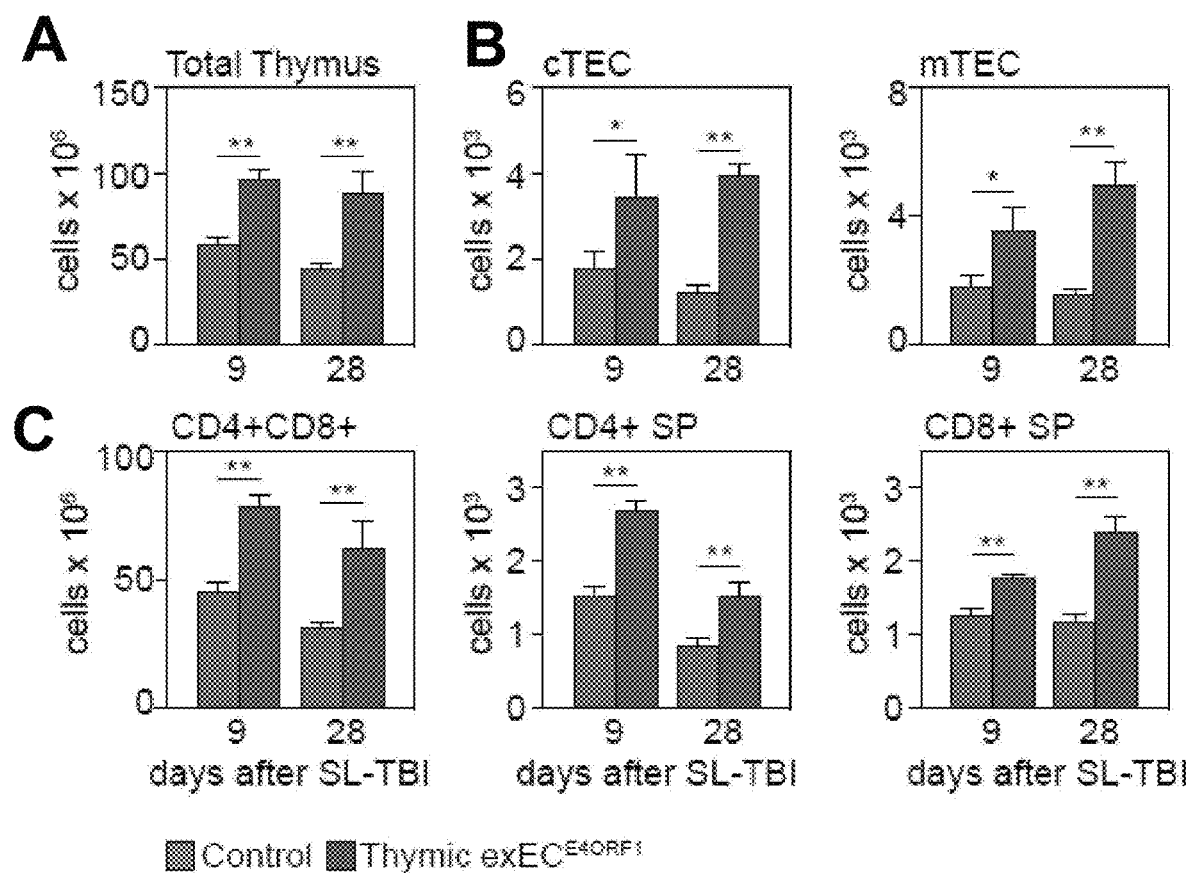
FIGS. 3A-3F shows that thymic ECs can be cultivated ex vivo and mediate enhanced thymic regeneration upon administration after damage. ECs were FACS sorted from the thymus based on expression of VE-cadherin. Isolated cells were transduced with the viral gene E4ORF1 (exEC$^{E4ORF1}$). In order to model immune injury we exposed 6-8 weeks old C57/B6 mice to a single dose of sublethal TBI (550cGy) and $1\times10^6$ exEC$^{E4ORF1}$ were administered intravenously at day 3 after SL-TBI (n=10-15/group). (A) Total thymic cellularity at days 9 and 28 after SL-TBI. (B) Number of cortical and medullary thymic epithelial cells (cTEC and mTEC, respectively). (C) Number of CD4+ CD8+ double positive (DP), CD3+CD4+CD8− or CD3+ CD4−CD8+ single positive (SP) thymocytes. (D) Thymic exEC$^{E4ORF1}$ were derived from transgenic mice with constitutive expression of firefly luciferase and administered at a dose of $2\times10^6$ cells at day 3 after SL-TBI. Luciferase expression was measured by BLI at 2 hours or 6 days after injection of cells. (E) exEC$^{E4ORF1}$ were derived from mice with GFP under the control of a chicken β-actin promoter and transplanted into 6 week old mice 3 days after SL-TBI. Thymus was harvested and GFP expression in the thymus assessed at day 9. (F) Thymic exEC$^{E4ORF1}$ were transplanted 24 hours after SL-TBI either directly into the thymus (IT, at a dose of $1\times10^4$ or $1\times10^5$) or intravenously (at a dose of $1\times10^6$). Total thymus cellularity was assessed at day 9. Bar graphs represent mean±SEM of at least 2 independent experiments. *, $p<0.05$; , $p<0.01$; *, $p<0.001$.
Figure 3D:
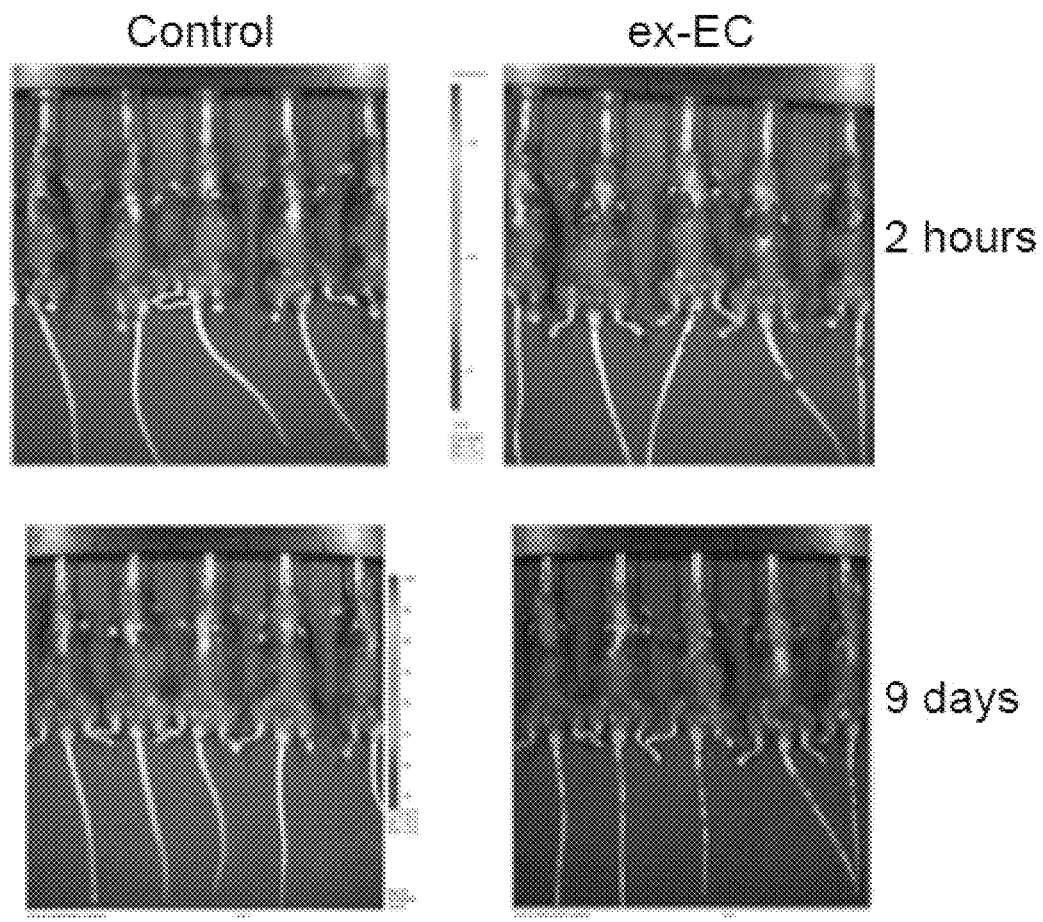
Figure 3E:
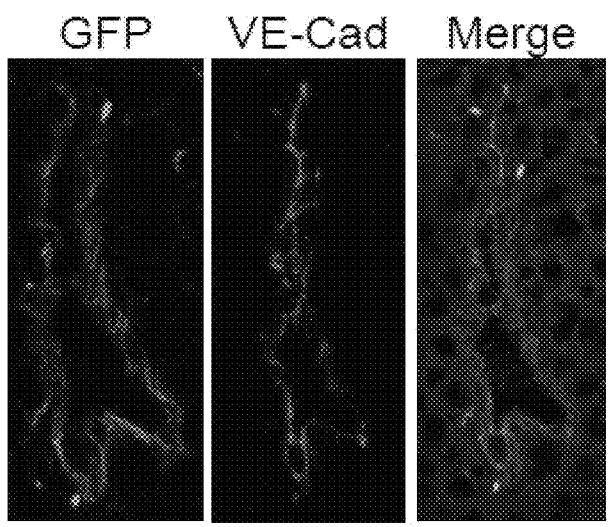
Figure 3F:
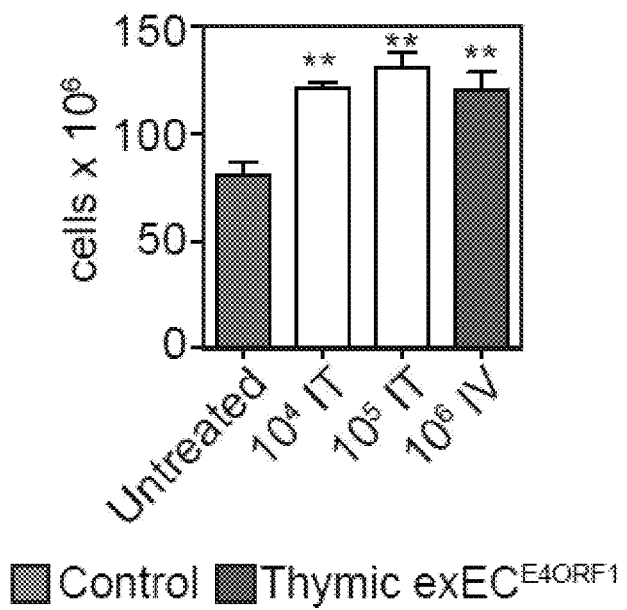

ECs may be FACS purified and transduced with a pro-survival adenoviral gene E4ORF1, and administered to orchestrate tissue regeneration. Exogenous E4ORF1-transduced thymic endothelial cells (exEC$^{E4ORF1}$) exhibit an EC phenotype expressing typical endothelial markers and show extensive vascular tube formation in vitro. When mice were transplanted with exEC$^{E4ORF1}$ following sublethal irradiation, the mice showed significantly increased thymic cellularity (FIG. 3a), including TECs (FIG. 3b) and thymocyte subsets (FIG. 3c) compared to control mice on days 9 and 28 after irradiation. It is thus contemplated that exEC$^{E4ORF1}$ are getting into the thymus to provide their regenerative effect. Little difference in thymic cellularity could be detected if mice were transplanted systemically intravenously or intrathymically; even if the number of exEC$^{E4ORF1}$ cells administered were 2 orders of magnitude fewer (FIG. 3f).

Figure 5A:
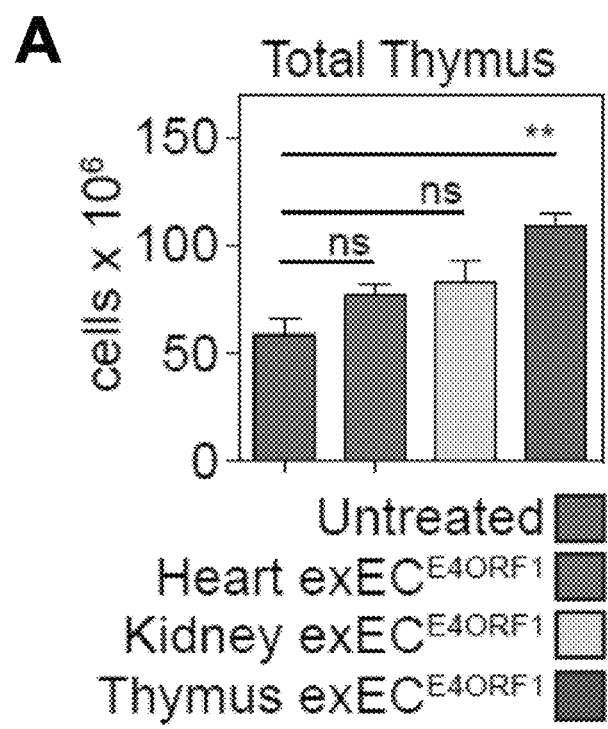
FIGS. 5A-5E shows that thymic regeneration mediated by exEC$^{E4ORF1}$ is restricted to those derived from the thymus. (A-B) ECs were FACS sorted from thymus, heart or kidney and transduced with the viral gene E4ORF1 as previously described. Cells were administered at day 3 after SL-TBI at a dose of $1\times10^6$ cells. (A) Total thymic cellularity at day 9 after SL-TBI. (B) Number of non-hematopoietic stromal cells including cortical and medullary thymic epithelial cells (cTEC and mTEC, respectively) and total number of ECs in the thymus at day 9 after SL-TBI. (C) Total number of CD4+CD8+ double positive (DP), CD3+CD4+CD8− or CD3+CD4−CD8+ single positive (SP) thymocytes at day 9 after SL-TBI. (D) Conditioned media (CM) was derived from thymus, heart or kidney exEC$^{E4ORF1}$ cultures and incubated with C9 cells for 24 hours when Foxn1 expression was assessed by qPCR. (E) Bmp4 expression in heart, kidney or thymus exEC$^{E4ORF1}$ measured by qPCR. Bar graphs represent mean±SEM of at least 2 independent experiments. *, $p<0.05$; , $p<0.01$, *, $p<0.001$.
Figure 5B:
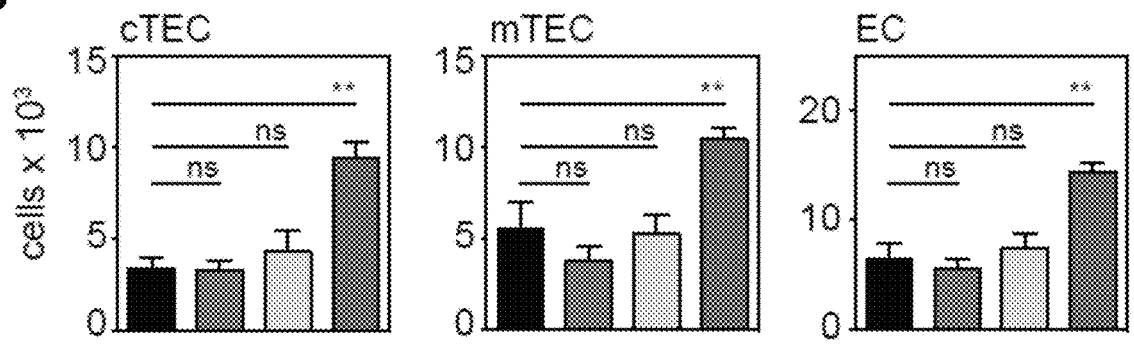
Figure 5C:
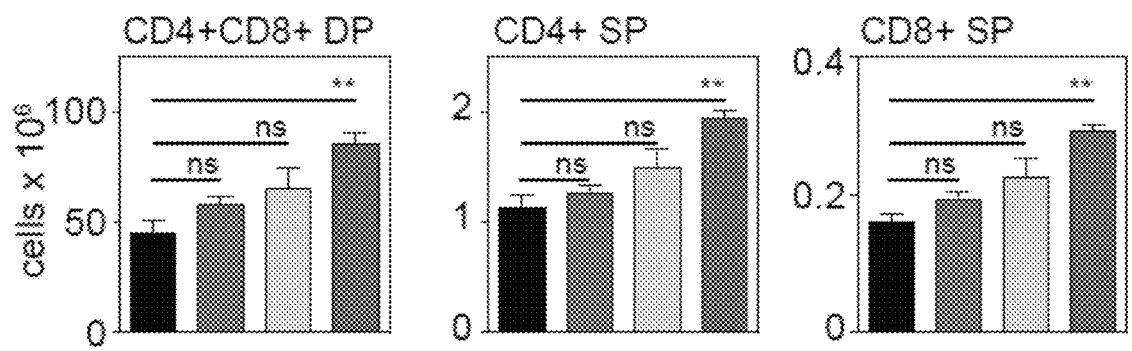

Although considerable benefit to thymic regeneration was observed when exEC$^{E4ORF1}$ were derived from thymic tissue, no effect on thymus regeneration was observed when exEC$^{E4ORF1}$ derived from cardiac or kidney endothelial cells (FIG. 5a), again including both TEC (FIG. 5b) and thymocyte (FIG. 5c) subsets. Interestingly, the number of ECs in the thymus was also significantly increased in mice that received exEC$^{E4ORF1}$. For example, exEC$^{E4ORF1}$ derived from the thymus are preferentially able to get into the thymus (FIG. 5b).

In one embodiment, a therapeutically effective amount of ex vivo-expanded thymic endothelial cells transduced with E4ORF1 (exEC$^{E4ORF1}$) can be administered to a subject to increase thymic cellularity following injury or damage to the thymus. Methods for the isolation and enrichment of endothelial cells, for example by fluorescence activated cell sorting are known in the art.

In one embodiment, a therapeutically effective amount of exEC$^{E4ORF1}$ is between $5 \times 10^3$ to $1 \times 10^7$ cells; in one embodiment between $1 \times 10^4$ and $1 \times 10^6$ cells; and in yet another embodiment, between $5 \times 10^4$ and $5 \times 10^5$ cells. Administration to a patient may be accomplished in any suitable route of administration well-known in the art that provides a patient with a therapeutically effective dosage, as indicated above.

BMP4 Mediates Regenerative Effect of ECs in Thymic Regeneration.

Bone morphogenic protein 4 (BMP4) may mediate the regenerative effect of ECs in thymic regeneration. BMP4 has been described during thymic ontogeny as inducing FOXN1 expression in the thymus and has also been shown to induce expression in hair follicles (17-19). BMP4 signals through a heterodimeric receptor composed of Bmpr1a and Bmpr2.

ECs may be potent producers of BMP4 after thymic damage, and this production may directly promote expression by cortical TECs of FOXN1, a key transcription factor involved in regeneration of the thymus.

Figure 4A:
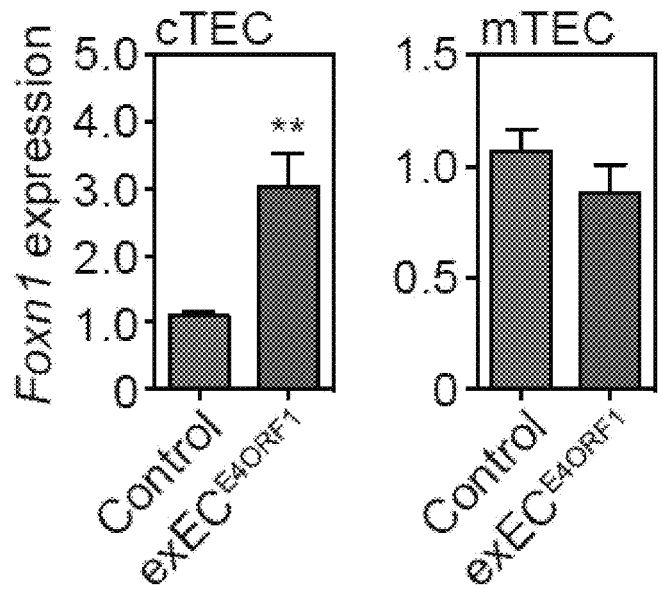
FIGS. 4A-4F shows that thymic ECs produce a soluble factor that promotes thymic regeneration after damage. (A) ECs were FACS sorted from the thymus based on expression of VE-cadherin. Isolated cells were transduced with the viral gene E4ORF1 (exEC$^{E4ORF1}$) as previously described. exEC$^{E4ORF1}$ derived from thymus were transplanted intravenously into 6 week old C57BL/6 mice 3 days after SL-TBI. Thymus was harvested 4 days later and cortical and medullary TECs were FACS purified and expression of Foxn1 was measured by qPCR. (B) Conditioned media (CM) derived from thymic exEC$^{E4ORF1}$ cultures was incubated with the cTEC cell line C9 for 24 hours when Foxn1 expression was assessed. The BMP inhibitor Noggin could inhibit the induction of Foxn1 by thymic exEC$^{E4ORF1}$ CM. BMP4 could also be shown to directly enhance Foxn1 expression in C9 cells and was inhibited by the BMP inhibitor, Noggin. (C) Cell subsets comprising approximately 99% of the known cellular subsets in the thymus were FACS purified and assessed for their expression of Bmp4 at steady-state by qPCR. (D) ECs were FACS purified from the thymus at day 4 after SL-TBI. Bmp4 expression was assessed by qPCR. (E-F) Thymus was harvested at days 4, 7 and 14 after SL-TBI and total BMP4 protein was measured by ELISA. (E) Absolute amount of BMP4 in the thymus. (F) BMP4 levels as a function of the total number of cells in the thymus. Bar graphs represent mean±SEM of at least 2 independent experiments. *, $p<0.05$; , $p<0.01$; *, $p<0.001$.

Upon administration of exEC$^{E4ORF1}$ in mice, a significant upregulation by TECs of FOXN1, a forkhead box transcription factor that is critical for TEC development, maintenance, and regeneration (7-11), may be observed. Intriguingly this increase may only be observed in the cTEC population (FIG. 4a), which is where a putative FOXN1-TEC progenitor population resides and becomes activated, upregulating FOXN1 during regeneration (8-10, 12-16).

Figure 4B:
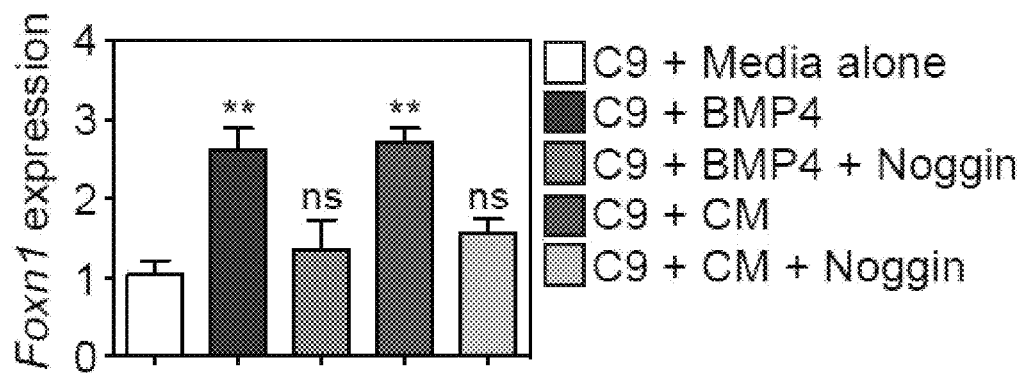
Figure 4C:
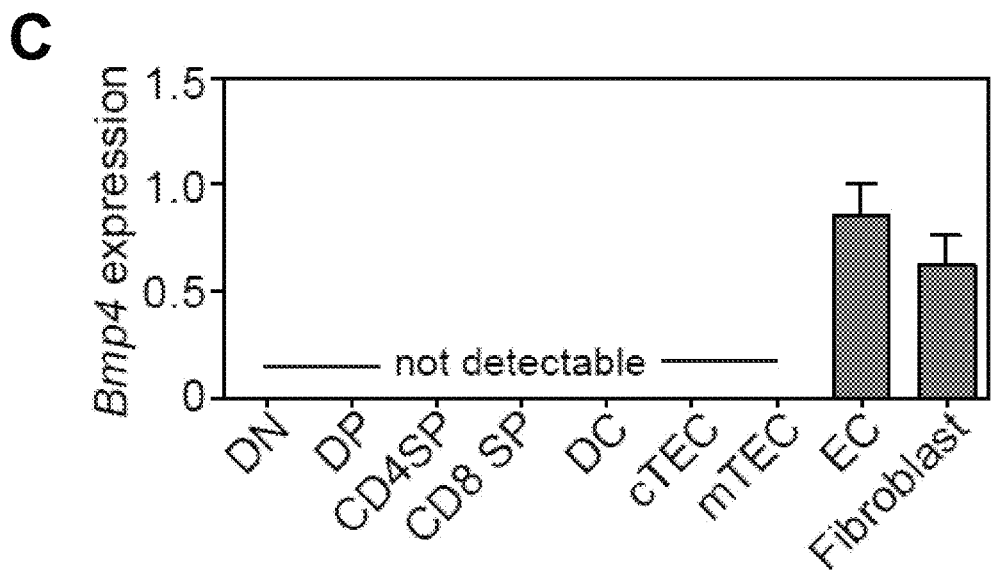
Figure 4D:
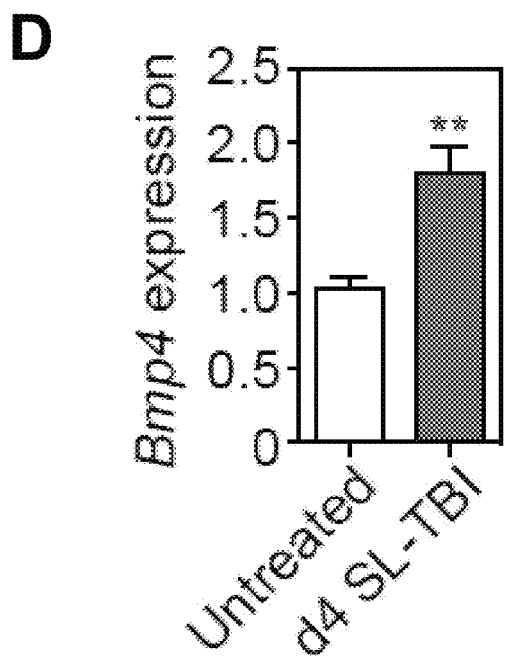

BMP4 may signal directly through TECs, promoting their regeneration, as well as acting in an autocrine fashion in ECs. BMP4 may be the mechanism by which exEC$^{E4ORF1}$ induces expression of FOXN1. After thymic damage caused by SL-TBI, significant upregulation of BMP4 expression by thymic ECs may be observed (FIG. 4d). Consistent with this, a significant increase in absolute amounts of BMP4 early after SL-TBI compared to control mice that were not irradiated (FIG. 4e) may be observed. Further, recombinant BMP4 may induce the upregulation of FOXN1 in cTEC cell line, C9 cells. However, this effect may be reversed by the BMP inhibitor Noggin (FIG. 4b). Thus, inhibition of BMP signaling may lead to significantly reduced thymic recovery after injury.

In another embodiment, a therapeutically effective amount of recombinant BMP4 may be administered to a patient to promote thymic regeneration in the patient following injury or damage to the thymus.

The administration of recombinant BMP4 may significantly aid thymic regeneration after injury. The administration of recombinant BMP4 may aid in boosting thymic function in aged individuals, and may be used as, for example, a vaccine adjuvant.

EXAMPLES

Cultivation of Thymic ECs Ex Vivo and Administration After Damage to Mediate Enhanced Thymic Regeneration.

To assess the regenerative potential of exEC$^{E4ORF1}$, young C57BL/6 mice were exposed to a sublethal dose of irradiation (550 cGy) and 72 h hours following irradiation $1 \times 10^6$ exEC$^{E4ORF1}$ were injected intravenously. Mice transplanted with exEC$^{E4ORF1}$ showed significantly increased thymic cellularity (FIG. 3a), including TECs (FIG. 3b) and thymocyte subsets (FIG. 3c) compared to control mice on days 9 and 28 after irradiation.

To test the engraftment and persistence of transplanted ECs, thymic exEC$^{E4ORF1}$ from transgenic mice with constitutive expression of firefly luciferase were generated (luc$^+$ exEC$^{E4ORF1}$). In the same model as described above, luc+ exEC$^{E4ORF1}$ could be detected as early as 2 hours post injection using a bioluminescence imaging system and appeared to localize to the thymic area (FIG. 3d). Consistent with this, using exEC$^{E4ORF1}$ derived from mice with GFP under the control of a chicken β-actin promoter, which ensures ubiquitous expression, GFP+ ECs could be detected in the thymus 6 days after transplant (FIG. 3e). Providing further evidence that exEC$^{E4ORF1}$ are getting into the thymus to provide their regenerative effect, little difference in thymic cellularity could be detected if mice were transplanted systemically intravenously or intrathymically; even if the number of exEC$^{E4ORF1}$ cells administered were 2 orders of magnitude fewer (FIG. 3f).

Thymic ECs Produce a Soluble Factor that Promotes Thymic Regeneration After Damage.

To test if the significant upregulation by TECs of FOXN1 is a direct effect of the exEC$^{E4ORF1}$, and if this was caused by a soluble factor produced by exEC$^{E4ORF1}$, conditioned media derived from thymic exEC$^{E4ORF1}$ cultures was incubated with the cTEC cell line, C9. After 24 hours FOXN1 expression was measured in C9 cells by qPCR. Consistent with our in vivo studies, significant upregulation of FOXN1 by C9 cells incubated with conditioned media derived from thymic exEC$^{E4ORF1}$ cultures was found (FIG. 4b).

Figure 4E:
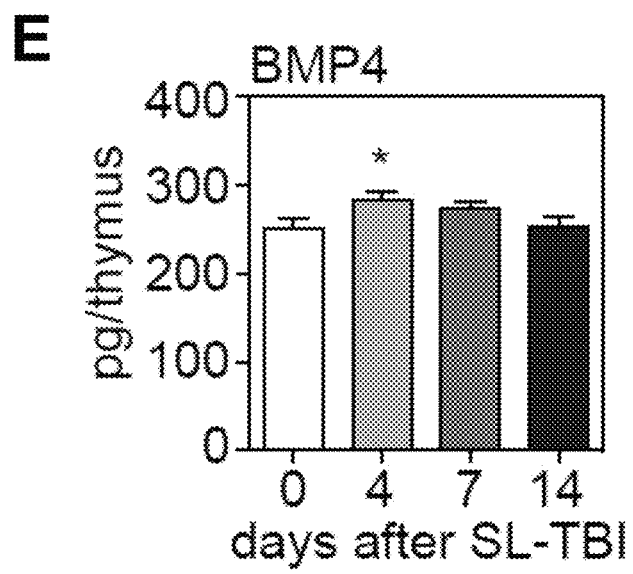
Figure 4F:
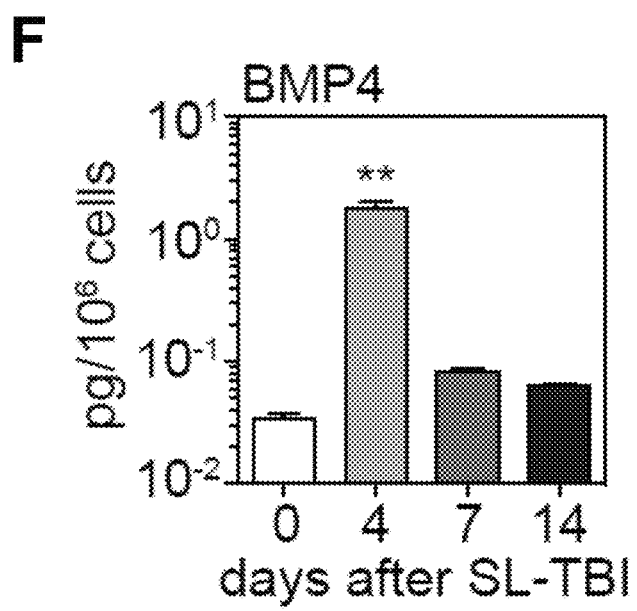

To explore if BMP4 might be the mechanism by which exEC$^{E4ORF1}$ induces expression of FOXN1, Noggin was added to wells that were incubated with CM from exEC$^{E4ORF1}$ cells. We found that Noggin could inhibit the induction of FOXN1 expression caused by CM from exEC$^{E4ORF1}$ cells (FIG. 4b). To explore what cells in the thymus express BMP4, populations from the thymus were FACS sorted and BMP4 expression was measured by qPCR. Although no detectable BMP4 expressed by any thymocyte subset, dendritic cells (DCs) or TECs was found, expression by endogenous ECs and Fibroblasts was seen (FIG. 4c). Moreover, after thymic damage caused by SL-TBI, significant upregulation of BMP4 expression by thymic ECs (FIG. 4d) was found. Consistent with this, a significant increase in absolute amounts of BMP4 was found early after SL-TBI compared to control mice that were not irradiated (FIG. 4e). This was striking given the significant decrease in thymic cellularity seen in irradiated mice (FIG. 2d) leading to a profound increase in the amount of IL-22 on a per cell basis (FIG. 4f).

Thymic Regeneration Mediated by exEC$^{E4ORF1}$ is Restricted to Those Derived from the Thymus.

Figure 5D:
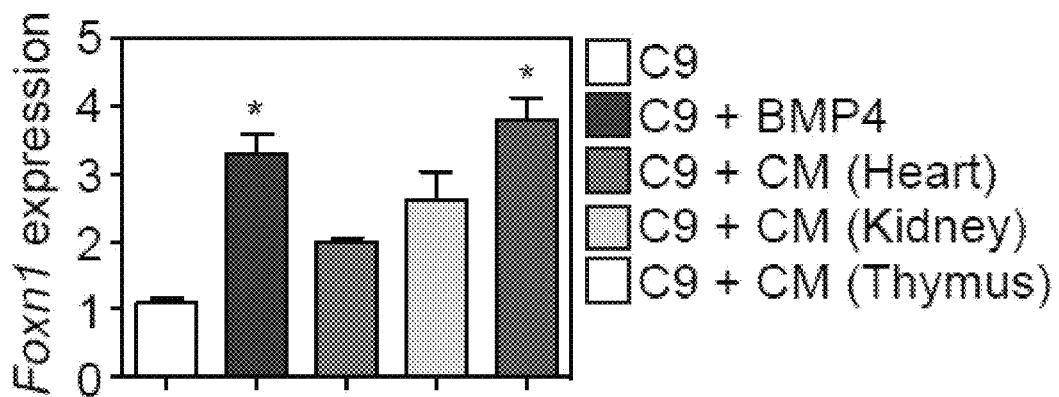
Figure 5E:
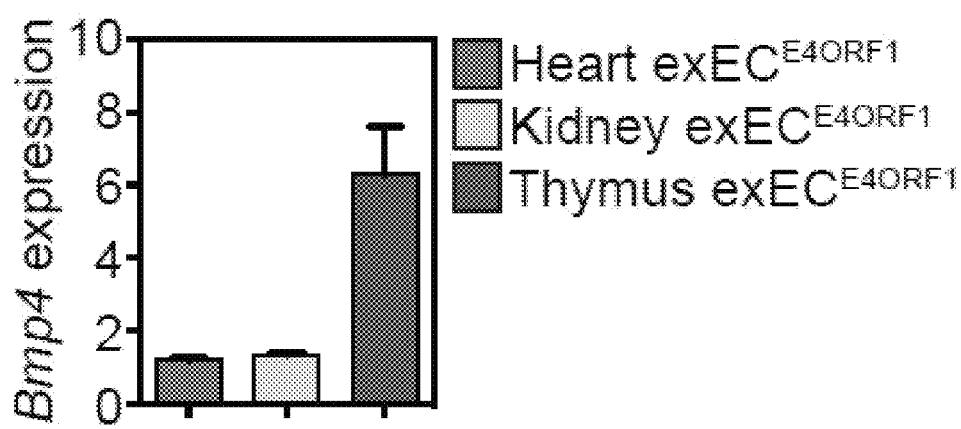

To assess the relative effect of exEC$^{E4ORF1}$ derived from different tissues on the induction of FOXN1 expression by TECs, conditioned media (CM) was derived from thymus, heart or kidney exEC$^{E4ORF1}$ cultures and incubated with C9 cells for 24 hours when FOXN1 expression was assessed by qPCR. Consistent with the in vivo findings suggesting the tissue-specificity of the regenerative response, only exEC$^{E4ORF1}$ derived from thymus were capable of inducing the expression of FOXN1 in C9 cells (FIG. 5d). Consistent with this, and the potential mechanism through BMP4 production, only low levels of BMP4 expression by heart and kidney exEC$^{E4ORF1}$ resulted in a six-fold increase in expression by thymic exEC$^{E4ORF1}$ (FIG. 5e).

BMP Receptors are Expressed Throughout the Thymus on Both Developing Thymocytes and the Non-Hematopoietic Stromal Compartment.

To explore which cells in the thymus could be targets of BMP4, receptor expression by various subsets in the thymus was evaluated. BMP4 signals through a heterodimeric receptor composed of Bmpr1a and Bmpr2. Interestingly, expression of both Bmpr1a and Bmpr2 across all stromal cell subsets within the thymus, including TECs and ECs (FIG. 6), was observed. BMP4 may signal directly through TECs, promoting their regeneration, as well as acting in an autocrine fashion in ECs.

BMP4 Produced by Thymic ECs Represents a Non-Redundant Angiocrine Factor Mediating Endogenous and Exogenous Thymic Regeneration.

To test the impact of BMP4 on thymic regeneration, exEC$^{E4ORF1}$ with BMP4 silenced by shRNA was generated. As confirmed by qPCR, BMP4 expression was reduced approximately 90% in exEC$^{E4ORF1}$ transduced with the shRNA compared to the scrambled control (FIG. 7a). In mice given SL-TBI and treated with scrambled or shRNA exEC$^{E4ORF1}$ on day 3, we found that the increase observed when exEC$^{E4ORF1}$ were administered was completely reversed if BMP4 was silenced in these cells (FIG. 7b). Further confirming this role of BMP4 in endogenous thymic regeneration, mice administered with a BMP inhibitor (Dorsomorphin dihydrochloride beginning 1 day prior to SL-TBI) exhibited significantly worse thymic recovery compared to PBS treated controls (FIG. 7d).

Prolonged thymic deficiency after cytoreductive conditioning is a significant clinical challenge. These studies not only identify a mechanism governing endogenous thymic regeneration, but also offer innovative therapeutic strategies for immune regeneration in patients whose thymus has been irrevocably damaged and for improving immune competence in patients whose thymic function has been compromised due to cytoreductive conditioning, infection or age.

Although the invention has been described with reference to a specific embodiment, this description is not meant to be construed in a limiting sense. The invention being thus described, it is apparent that the same can be varied in many ways. Such variations are not to be regarded as a departure from the spirit and scope of the present invention, and all such modifications, alternatives, and equivalents as would be obvious to one skilled in the art are intended to be included within the scope of the following claims.

REFERENCES

1. Gruver A L, Sempowski G D. 2008. Cytokines, leptin, and stress-induced thymic atrophy. *Journal of Leukocyte Biology* 84: 915-23
2. van den Brink M R, Alpdogan O, Boyd R L. 2004. Strategies to enhance T-cell reconstitution in immunocompromised patients. *Nat Rev Immunol* 4: 856-67
3. Cuddihy A R, Suterwala B T, Ge S, Kohn L A, Jang J, Andrade J, Wang X, Crooks G M. 2012. Rapid thymic reconstitution following bone marrow transplantation in neonatal mice is VEGF-dependent. *Biol Blood Marrow Transplant* 18: 683-9
4. Seandel M, Butler J M, Kobayashi H, Hooper A T, White I A, Zhang F, Vertes E L, Kobayashi M, Zhang Y, Shmelkov S V, Hackett N R, Rabbany S, Boyer J L, Rafii S. 2008. Generation of a functional and durable vascular niche by the adenoviral E4ORF1 gene. *Proc Natl Acad Sci USA* 105: 19288-93
5. Ding B S, Nolan D J, Guo P, Babazadeh A O, Cao Z, Rosenwaks Z, Crystal R G, Simons M, Sato T N, Worgall S, Shido K, Rabbany S Y, Rafii S. 2011. Endothelial-derived angiocrine signals induce and sustain regenerative lung alveolarization. *Cell* 147: 539-53
6. Kobayashi H, Butler J M, O'Donnell R, Kobayashi M, Ding B S, Bonner B, Chiu V K, Nolan D J, Shido K, Benjamin L, Rafii S. 2010. Angiocrine factors from Akt-activated endothelial cells balance self-renewal and differentiation of haematopoietic stem cells. *Nat Cell Biol* 12: 1046-56
7. Nehls M, Kyewski B, Messerle M, Waldschutz R, Schuddekopf K, Smith A J, Boehm T. 1996. Two genetically separable steps in the differentiation of thymic epithelium. *Science* 272: 886-9
8. Chen L, Xiao S, Manley N R. 2009. Foxn1 is required to maintain the postnatal thymic microenvironment in a dosage-sensitive manner. *Blood* 113: 567-74
9. Bleul C C, Corbeaux T, Reuter A, Fisch P, Monting J S, Boehm T. 2006. Formation of a functional thymus initiated by a postnatal epithelial progenitor cell. *Nature* 441: 992-6
10. Bredenkamp N, Nowell C S, Blackburn C C. 2014. Regeneration of the aged thymus by a single transcription factor. *Development* 141: 1627-37
11. Zook E C, Krishack P A, Zhang S, Zeleznik-Le N J, Firulli A B, Witte P L, Le P T. 2011. Overexpression of Foxn1 attenuates age-associated thymic involution and prevents the expansion of peripheral CD4 memory T cells. *Blood* 118: 5723-31
12. Bredenkamp N, Ulyanchenko S, O'Neill K E, Manley N R, Vaidya H J, Blackburn C C. 2014. An organized and functional thymus generated from FOXN1-reprogrammed fibroblasts. *Nat Cell Biol* advance online publication
13. Corbeaux T, Hess I, Swann J B, Kanzler B, Haas-Assenbaum A, Boehm T. 2010. Thymopoiesis in mice depends on a Foxn1-positive thymic epithelial cell lineage. *Proc Natl Acad Sci USA* 107: 16613-8
14. Sun L, Guo J, Brown R, Amagai T, Zhao Y, Su D M. 2010. Declining expression of a single epithelial cell-autonomous gene accelerates age-related thymic involution. *Aging Cell* 9: 347-57
15. Ucar A, Ucar O, Klug P, Matt S, Brunk F, Hofmann Thomas G, Kyewski B. 2014. Adult Thymus Contains FoxN1—Epithelial Stem Cells that Are Bipotent for Medullary and Cortical Thymic Epithelial Lineages. *Immunity* 41: 257-69
16. Wong K, Lister Natalie L, Barsanti M, Lim Joanna M C, Hammett Maree V, Khong Danika M, Siatskas C, Gray Daniel H D, Boyd Richard L, Chidgey Ann P. 2014. Multilineage Potential and Self-Renewal Define an Epithelial Progenitor Cell Population in the Adult Thymus. *Cell Reports* 8: 1198-209
17. Tsai P T, Lee R A, Wu H. 2003. BMP4 acts upstream of FGF in modulating thymic stroma and regulating thymopoiesis. *Blood* 102: 3947-53
18. Cai J, Lee J, Kopan R, Ma L. 2009. Genetic interplays between Msx2 and Foxn1 are required for Notch1 expression and hair shaft differentiation. *Dev Biol* 326: 420-30
19. Bleul C C, Boehm T. 2005. BMP signaling is required for normal thymus development. *Journal of Immunology* 175: 5213-21

We claim:

1. A method to promote thymic regeneration and/or enhance thymic epithelial cell function following injury or damage to the thymus, the method comprising exposing the thymus to an effective amount of thymus-derived endothelial cells that secrete BMP4.

2. The method of claim 1, wherein the injury or damage to the thymus is due to aging, stress, infection, cytoreductive chemotherapy, corticosteroids, or radiation.

3. The method of claim 1, wherein the thymic endothelial cells are transduced with a viral gene.

4. The method of claim 3, wherein the viral gene is an adenoviral gene.

5. The method of claim 4, wherein the adenoviral gene is E4ORF1.

6. The method of claim 1, wherein the endothelial cells are $CD45^-VE\text{-}Cadherein^+$.

7. The method of claim 1, wherein BMP4 secreting thymic endothelial cells are administered to the thymus 1 day before the onset of injury or damage.

8. The method of claim 1, wherein BMP4 secreting thymic endothelial cells are administered to the thymus from 1 to 5 days following damage or injury.

9. The method of claim 1, wherein BMP4 secreting thymic endothelial cells are administered intravenously.

10. The method of claim 1, wherein BMP4 secreting thymic endothelial cells are administered intrathymically.

11. The method of claim 1, wherein the promotion of thymic regeneration is characterized by an increased number of mature functional T-cells in the thymus.

12. The method of claim 1, wherein the enhanced thymic epithelial cell function is characterized by an increased number of mature functional T-cells in the thymus.

* * * * *